(12) United States Patent
Eberwein et al.

(10) Patent No.: US 11,484,425 B2
(45) Date of Patent: Nov. 1, 2022

(54) APPARATUS AND METHOD FOR STABILIZING A HUMAN ANATOMICAL JOINT

(71) Applicant: Stoko Design Inc., Vancouver (CA)

(72) Inventors: Zachary Eberwein, North Vancouver (CA); Scott Morgan, North Vancouver (CA); Cameron Massullo, North Vancouver (CA)

(73) Assignee: Stoko Design Inc., Vancouver (CA)

( * ) Notice: Subject to any disclaimer, the term of this patent is extended or adjusted under 35 U.S.C. 154(b) by 592 days.

(21) Appl. No.: 16/216,668

(22) Filed: Dec. 11, 2018

(65) Prior Publication Data

US 2019/0374361 A1    Dec. 12, 2019

Related U.S. Application Data

(60) Provisional application No. 62/640,513, filed on Mar. 8, 2018, provisional application No. 62/599,675, filed on Dec. 15, 2017.

(51) Int. Cl.
| | | |
|---|---|---|
| *A61F 5/01* | (2006.01) | |
| *A41D 13/12* | (2006.01) | |
| *A63B 71/12* | (2006.01) | |

(52) U.S. Cl.
CPC ........ *A61F 5/0109* (2013.01); *A41D 13/1254* (2013.01); *A61F 2005/0155* (2013.01);
(Continued)

(58) Field of Classification Search
CPC ............ A61F 5/0109; A61F 2005/0155; A61F 2005/0167; A61F 2005/0179;
(Continued)

(56) References Cited

U.S. PATENT DOCUMENTS

| | | | |
|---|---|---|---|
| 4,116,236 A | | 9/1978 | Albert |
| 4,216,547 A | * | 8/1980 | Picchione .......... A41D 13/0543 2/22 |

(Continued)

OTHER PUBLICATIONS

Canadian Patent Office, International Search Report, dated Mar. 6, 2019 (PCT/CA2018/051591).

(Continued)

*Primary Examiner* — Ophelia A Hawthorne
(74) *Attorney, Agent, or Firm* — Kevin R. Erdman; Brannon Sowers & Cracraft PC

(57) ABSTRACT

A garment of the present invention comprises a closed tensionable loop for stabilizing a human knee. The loop is arranged to freely move along a conduit within the garment and is provided with a tensioner. The conduit crosses over itself between the lateral and a medial side on the anterior of the leg at least one of above and below the knee to provide compression on the ligaments of the knee when the loop is tensioned. The conduit circles the lower leg at a distal region of the triceps surae, thereby providing an anchor to the lower leg. An anchor is provided at or above the thigh. A method for stabilizing the knee using the tensionable loop involves positioning the garment so as to ensure that the conduit follows a predetermined path on the leg that places the loop over at least one of the two collateral ligaments of the knee and the tensioner is operated to adjust the compression on the ligaments.

21 Claims, 15 Drawing Sheets

(52) U.S. Cl.
CPC ............... *A61F 2005/0167* (2013.01); *A61F 2005/0179* (2013.01); *A61F 2005/0181* (2013.01); *A63B 71/1225* (2013.01)

(58) Field of Classification Search
CPC ........ A61F 2005/0181; A41D 13/1254; A41D 13/0543; A41D 31/185; A63B 71/1225
See application file for complete search history.

(56) References Cited

U.S. PATENT DOCUMENTS

| | | | | |
|---|---|---|---|---|
| 4,862,523 | A * | 9/1989 | Lipov | A61F 13/08 2/409 |
| 8,296,864 | B2 * | 10/2012 | Torry | A41D 13/065 2/69 |
| 2006/0130215 | A1 | 6/2006 | Torry | |
| 2010/0095422 | A1 | 4/2010 | Lopez et al. | |
| 2015/0074865 | A1 | 3/2015 | Yamada et al. | |
| 2018/0338547 | A1 | 11/2018 | Celestrin Carmona | |

OTHER PUBLICATIONS

Canadian Patent Office, International Search Written Opinion, dated Mar. 6, 2019 (PCT/CA2018/051591).

\* cited by examiner

APPARATUS AND METHOD FOR STABILIZING A HUMAN ANATOMICAL JOINT

CROSS-REFERENCE TO RELATED APPLICATIONS

The present application claims priority under § 35 U.S.C. 119(e) from U.S. Provisional Patent Application Ser. Nos. 62/599,675 and 62/640,513; filed Dec. 15, 2017, and Mar. 8, 2018, respectively; the disclosures of which are incorporated in their entirety herein.

BACKGROUND OF THE INVENTION

Field of the Invention

This present invention relates to the medical field as exemplified by IPC class A61 and more particularly to apparatus and associated methods for stabilizing articulating joints of the human body, including devices adapted to facilitate walking. In one aspect, it relates to an apparatus for stabilizing the human knee and the operation of such an apparatus configured and arranged for treating damaged ligaments in the knee.

Description of the Related Art

Orthopedic braces are used to stabilize joints between the limbs of the human anatomy in cases where the joints or the limbs articulating about them have sustained damage. Braces have been employed to stabilize knees, ankles, elbows and wrists in this way. The brace is applied to reduce strain on the injured limb or joint while permitting the limb or joint to still perform its function, thereby minimizing the risk of further damage.

Several knee brace products have been developed to more specifically protect the ligaments of the knee, including the anterior cruciate ligament (ACL), posterior cruciate ligament (PCL), and medial collateral ligament (MCL). These are the ligaments most often damaged in when knees are overstrained, particularly by individuals involved in strenuous sporting activity. The lateral collateral ligament (LCL) may also sometimes become strained. The brace products for protecting these ligaments vary greatly in technology, function, and efficacy.

Some products are focused on providing mechanical encapsulation that still allows articulation of the joint. Such products tend to involve rather heavy hinge mechanisms and are generally bulky and not particularly aesthetic. At the other extreme there are several products that assume the form of a garment, different forms of such garments employing different technologies to produce compressive forces in the general vicinity of the knee in an attempt to stabilize it and protect the above ligaments. Some garments fall short in providing enough compression. Others provide adequate overall compression but do not direct the compression to key anatomical areas.

SUMMARY OF THE INVENTION

In a first aspect, a garment is presented that is arranged for enveloping at least in part an articulating joint of a human body, the garment comprising one or more tension members each disposed longitudinally along a corresponding predetermined curved three-dimensional spatial path within or on a matrix of a garment material, the corresponding predetermined paths spatially relating the one or more tension members to at least one natural ligament of the joint. The one or more tension members may each comprise one or more strands of a substantially longitudinally inextensible material; and the garment material may comprise conduits disposed within or on the garment material and arranged to receive the one or more strands of each tension member. Each conduit may a lower coefficient of friction with respect to the strands than the coefficient of friction of the garment material with respect to the strands. Each conduit may comprise one or more tube of material different from the garment material, the tubes arranged lengthwise along the predetermined three-dimensional spatial path of the corresponding tension member.

The garment may further comprise at least one tensioner disposed in line with at least one of the one or more tension members for tensioning the at least one tension member. At least one of the one or more tension members may further comprise at least one tension regulator disposed for balancing tension differences between different strands of the at least one tension member.

When the articulating joint is a knee with a patella in a leg of the human body, the path of at least one of the one or more tension members may comprise a lateral segment disposed to extend generally vertically proximate and lateral to the patella and a medial segment disposed to extend generally vertically proximate and medial to the patella. The garment may further comprise at least one portion of inextensible fabric connecting the medial segment of the at least one tension member to the lateral segment of the at least one tension member around the posterior of the leg.

The lateral and medial segments of the at least one tension member may further be disposed to cross over each other above and below the knee at respectively upper and lower crossover points. The garment may further comprise at least one of a portion of inextensible fabric connecting the medial segment of the at least one tension member to the lateral segment of the at least one tension member over the anterior of the knee above the upper crossover point and a portion of inextensible fabric connecting the medial segment of the at least one tension member to the lateral segment of the at least one tension member over the anterior of the knee below the lower crossover point.

In general, in the case of the articulating joint being a knee, the garment may comprise a portion of inextensible fabric laterally joining two segments of the tension member in tension with respect to each other horizontally over the leg.

The garment may further comprise a belt disposed for tightening the garment about a waist of the human body and a stabilizing connector connecting the at least one tension member to the belt, wherein the stabilizing connector is composed of a substantially inextensible material.

The three dimensional spatial path of at least one tension member may extend around a limb articulating at the joint. The three-dimensional spatial path of at least one tension member may be arranged so that tension in the at least one tension member produces or exerts a compressive force proximate the joint. The at least one longitudinal portion of the one or more tension members may comprise a length of substantially inextensible fabric.

In another aspect, a garment is presented that comprises a closed tensionable loop arranged to freely move along a conduit within or on the garment, wherein the conduit is arranged to cross over itself between a lateral and a medial side on the anterior of a leg of the user at least one of above and below a knee of the leg. In some embodiments, the conduit is arranged to cross over itself between a lateral and a medial side on the anterior of a leg of the user both above and below a knee of the leg. The tensionable loop is disposed in or on the garment for applying pressure to at least one of a lateral collateral ligament and a medial collateral ligament of the user when the garment is worn by the user and the tensionable loop is tensioned. The garment may further comprise a tensioner disposed for tensioning the tensionable loop. The garment may further comprise a belt disposed to fit around the waist of the user and the tensionable loop may be anchored to the belt. The conduit may be arranged along a path that circles the leg at a distal region of a triceps surae of the leg.

The garment may further comprise an anchor member and the tension member and anchor member may jointly at least partially, or in major part, encircle the thigh. In other embodiments, the tension member at least partially, or in major part, encircles the thigh.

The tensionable loop may comprise a tension member extending along the conduit sandwiched between layers of low friction material. The garment may be fashioned from a garment material and the conduit may be contained within the garment material and be laterally demarcated by stitching. The stitching may comprise a low friction fiber. The tensionable loop may comprise a tension member extending along the conduit and the conduit may comprise a low friction tube, which may be a collated tube. The tensionable loop may comprise a tension member made of a substantially longitudinally inextensible material and the inextensible material may be flexible.

In a further aspect, a method is presented for stabilizing a knee of a human user leg, comprising: applying around a knee of the user a wearable garment comprising a garment leg, a garment knee, a tensioner and a closed tensionable loop arranged around the leg of the garment to freely move longitudinally along a conduit within or on the garment, wherein the conduit is arranged to cross over itself between a lateral and a medial side on the anterior of the garment leg above and below the knee of the garment and the tensioner is disposed and arranged for adjusting a tension the loop; and operating the tensioner to adjust a tension in the loop.

The applying may comprise: arranging the garment on the user to position a first portion of the loop against a distal region of a triceps surae of the user leg; positioning a second portion of the loop on or above a thigh of the user leg; and positioning on the medial and lateral sides of a patella of the user leg proximate two collateral ligaments of the user knee third and fourth portions of the loop located on the loop between the first and second portions. The positioning of the second portion of the loop may comprise positioning the second portion of the loop against a posterior of the thigh of the user leg.

In a further aspect, a method is provided for manufacturing a wearable garment for stabilizing a knee of a user, the method comprising: forming a garment covering at least in part at least a knee, an adjoining triceps surae, and a distal portion of an adjoining thigh; establishing at least one of in and on the garment a conduit for receiving a tensionable loop, the conduit arranged to cross over itself between a lateral and a medial side on the anterior of the garment at least one of above and below the garment knee; threading along a path through the conduit a tensionable member; establishing one of in and on the loop a tensioner for adjusting a tension the loop.

Threading the tensionable member may comprise threading a tensionable member that is substantially inextensible. Threading the tensionable member may comprise threading a tensionable member that is flexible and substantially inextensible. Threading the tensionable member may comprise threading a tensionable member made from one or more of PTFE, stainless steel, Nylon®; Kevlar®; one or more ultra high molecular weight polyethylene based fiber, a fiber with a diamond weave. Threading a tensionable member made from the fiber with a diamond weave may comprise threading a tensionable member made from one of cotton, polyester, polypropylene, and Technora®.

Establishing the conduit may comprise arranging the conduit to cross over itself above and below the knee. Forming the garment may comprise extending the garment to a waist of the user, forming a belt around the waist. Establishing the tensioner may comprise establishing the tensioner on the belt. Establishing the tensioner in or on the loop may comprise establishing the tensioner on a thigh of the garment.

In a further embodiment, a wearable garment is presented for stabilizing a knee of a user comprising: a closed tensionable loop arranged to freely move along a conduit disposed within or on the garment, the conduit extending along a conduit path having relative to the knee a lateral portion and a medial portion; and an adjustable tensioner in or on the loop for adjusting a tension in the loop; wherein the lateral and medial portions of the conduit path pass a patella of the user knee proximate the lateral and medial collateral ligaments of the user knee respectively and in which the lateral and medial portions of the conduit path closely approach each other at least one point, the at least one point being at least one of below and above the user knee.

The lateral and medial portions of the conduit path may closely approach each other at a first point below the user knee and at a second point above the user knee. The tensionable loop may be disposed for applying pressure to at least one of the lateral collateral ligament and a medial collateral ligament of the user when the garment is worn by the user and the tensionable loop is tensioned. The conduit may be arranged along a path that substantially circles the leg at a distal region of a triceps surae of the leg. The tensionable loop may comprise a tension member extending along the conduit. The tensioner may be disposed on the thigh of the user. The tension member may be made of a substantially longitudinally inextensible material and the material may be flexible. The conduit may comprise a low friction tube and the tube may be collated.

In a further aspect a method is presented for manufacturing a wearable garment for stabilizing a knee of a user, the method comprising: forming a garment covering at least in part at least a knee, an adjoining triceps surae, and a distal portion of an adjoining thigh; establishing at least one of in and on the garment a conduit for receiving a tensionable loop, the conduit extending along a conduit path having relative to the knee a lateral portion and a medial portion, the lateral and medial portions of the conduit path closely approaching each other at least one point, the at least one point being at least one of below and above the user knee; threading along a path through the conduit a tensionable member; establishing one of in and on the loop a tensioner for adjusting a tension the loop.

Threading the tensionable member may comprise threading a tensionable member that is substantially inextensible. Threading the tensionable member may comprise threading a tensionable member that is flexible and substantially inextensible. Threading the tensionable member may comprise threading a tensionable member made from one or more of PTFE, stainless steel, Nylon®; Kevlar®; one or more ultra high molecular weight polyethylene based fiber, a fiber with a diamond weave.

Threading a tensionable member made from the fiber with a diamond weave may comprise threading a tensionable member made from one of cotton, polyester, polypropylene, and Technora®. Establishing the conduit may comprise arranging the conduit to have the lateral and medial portions of the conduit path closely approaching each other below and above the user knee. Forming the garment may comprise extending the garment to a waist of the user, forming a belt around the waist, in which establishing the tensioner comprises establishing the tensioner on the belt. Establishing the tensioner in or on the loop may comprise establishing the tensioner on a thigh of the garment.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
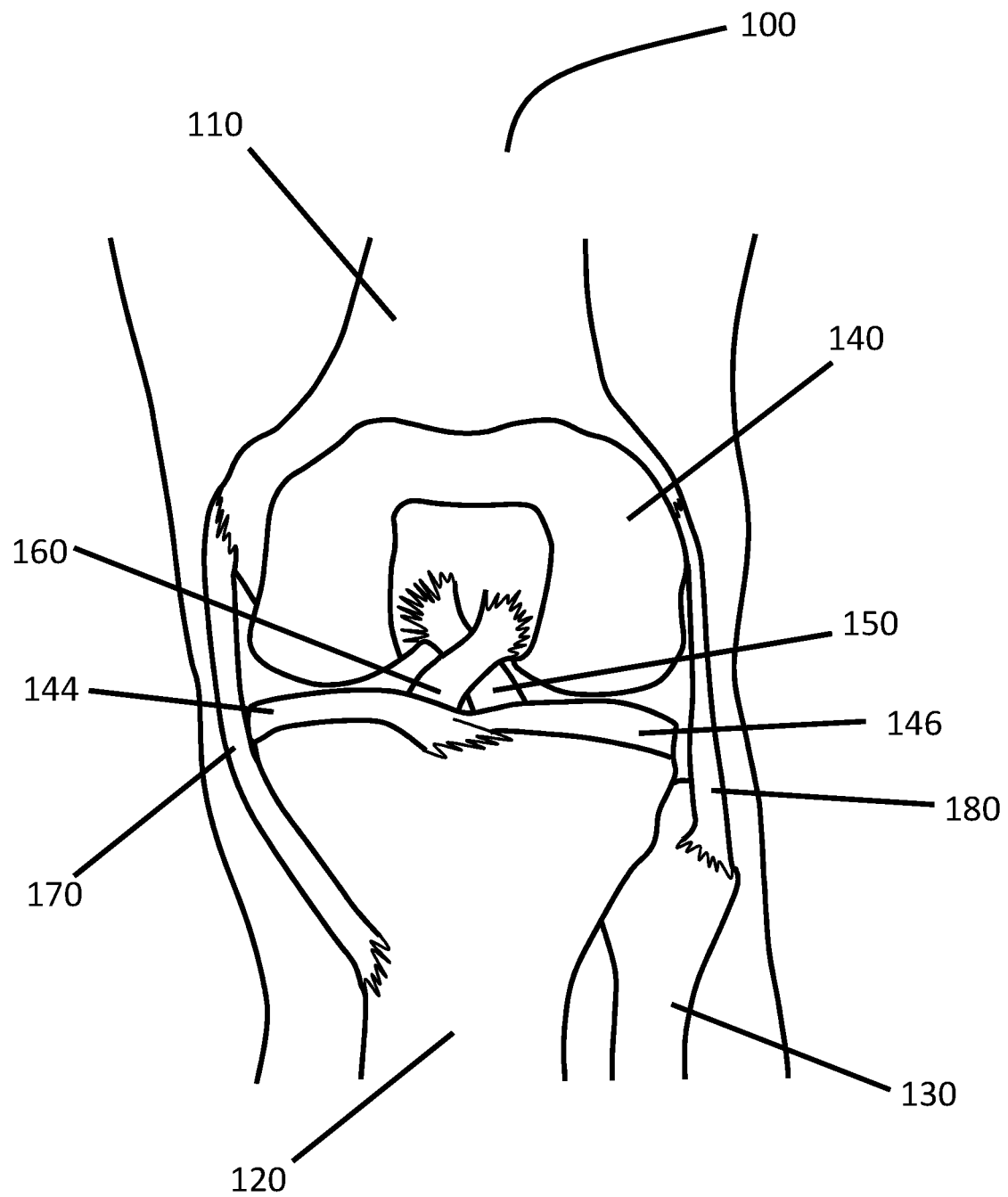
FIG. 1 is a drawing showing the general structure of the human left knee with the patella and its adhesions deleted for the sake of clarity.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The present invention relates to a garment incorporating a brace arrangement for an articulating joint of a human body. The brace comprises tension members each disposed longitudinally along a corresponding predetermined curved three-dimensional spatial path within or on a matrix of the garment material, the corresponding predetermined paths spatially relating the one or more tension members to at least one natural ligament of the joint. In order to describe the garment and brace, we consider first the human knee as shown in FIG. 1.

FIG. 1 shows internal knee portion 100 of a human left leg as viewed from front or anterior, but with the patella or knee cap and its various adhesions removed for the sake of clarity of the internal structure of this particular joint. Major bones of the leg are shown as femur 110, tibia 120 and fibula 130. The portions of these bones that contact one another during articulation are provided with articular cartilage 140, the two portions of the cartilage on tibia 120 being medial meniscus 144 and lateral meniscus 146. The bones are stabilized with respect to one another by strategically placed ligaments that hold them together. These include posterior cruciate ligament (PCL) 150 and anterior cruciate ligament (ACL) 160 binding together the interacting faces of femur 110 and tibia 120, and medial collateral ligament (MCL) 170 and lateral collateral ligament (LCL) 180 binding respectively tibia 120 and fibula 130 to respectively the medial and lateral portions of the head of femur 110.

In the following description, various embodiments of an inventive garment are shown as disposed on a human from a middle section of the body and down the leg, with the entire lower portion of the body including the feet being covered by the garment. In actual embodiments, the garment may or may not extend all the way up to or past the waist, or completely covering the feet. Such variations in the configuration of a garment in accordance with the present invention may be dictated by style, manufacturing methods, and/or particular configurations for individual situations. Accordingly, the following detailed description of embodiments represents only a small fraction of the possible variations of such garments.

Figure 2:
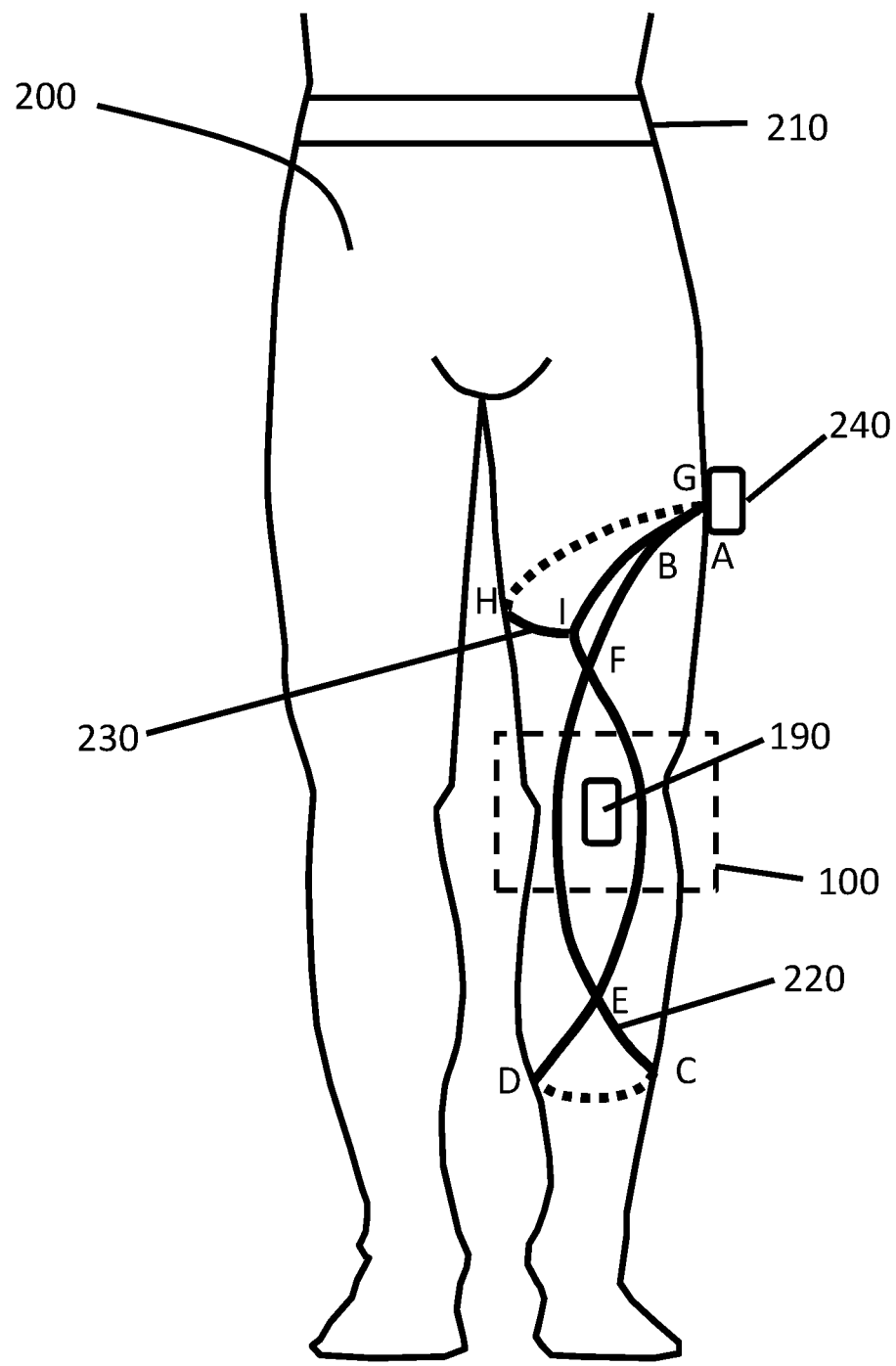
FIG. 2 is a drawing of a first embodiment of a bracing garment for bracing the human left knee.

We turn now to a first embodiment of a brace garment shown in FIG. 2, in which the knee joint of FIG. 1 is dressed in garment 200 comprising belt 210, tension member 220, anchor member 230, and tensioner 240. Broken rectangle 100 indicates the region of the left leg shown in FIG. 1. Tension member 220 follows a predetermined path related to the disposition of ligaments 150, 160, 170 and 180 described above. Proceeding from tensioner 240 at point A, the path proceeds to point B where tension member 220 splits in its path to form a single closed loop path. The path proceeds from the left lateral side to pass patella 190 of the left leg on the medial side before curving around again to reach the lateral side of the left leg at point C at the distal portion of the triceps surae (the collection of muscles of the human calf), from where it proceeds around the back of the leg once more (shown in broken line) to the medial side of the left leg at point D. It then proceeds from point D to cross over its own path at point E in order to proceed along a curved path around the lateral side of patella 190. After crossing over itself at point F, the path curves sharply to the left lateral side to arrive at point B where it rejoins itself. At crossover points E and F, the outgoing and incoming portions of tension member 220 are independent, they do not join each other and are arranged to move as freely from each other as possible.

The path of anchor member 230 extends from tensioner 240 at point G around the back of the thigh (shown as a broken line) to point H on the medial side and then to point I where it terminates proximate tension member 220. The path of tension member 220 makes a sharp curve at point I. The exact way in which anchor member 230 and tension member 220 are arranged at point I is described in more detail below. For the present purposes it suffices to point out that the path of anchor member 230 and the path of tension member 220 jointly form a closed loop around the thigh to anchor brace garment 200 to the thigh. That is, with reference also to further embodiments below, tension member 220 and anchor member 230 together fully encircle the thigh irrespective of how any anchoring function is distributed between tension member 220 and anchor member 230. The loop from point C to point D to point E formed by the path of tension member 220 at the calf of the leg similarly anchors brace garment 200 to the calf.

In operation, tension member 220 may have its tension adjusted by the wearer of garment 200 via tensioner 240. Similarly, in embodiments in which anchor member 230 extends along its path within a conduit, as addressed in more detail below, anchor member 230 may have its tension adjusted by tensioner 240. In other embodiments, anchor member 230 may be comprised of a material that is longitudinally inextensible and tensioner 240 may in such embodiments be disposed on the inextensible material so that tensioning tension member 220 also tensions anchor member 230.

Tensioner 240 may be implemented in a variety of embodiments, including without limitation ratchet arrangements and lug screw arrangements. Any arrangement capable of establishing longitudinal tension in tension member 220 and compatible with human operation is suitable.

The embodiment of FIG. 2 specifically shows tension member 220 crossing over itself both above and below the knee. In a more general embodiment it needs only cross over itself either above or below the knee. However, there is merit in the downward and upward portions of the path of tension member 220 approaching each other on the side of the knee opposing that on which the tension member 220 in fact does cross over itself.

Figure 3:
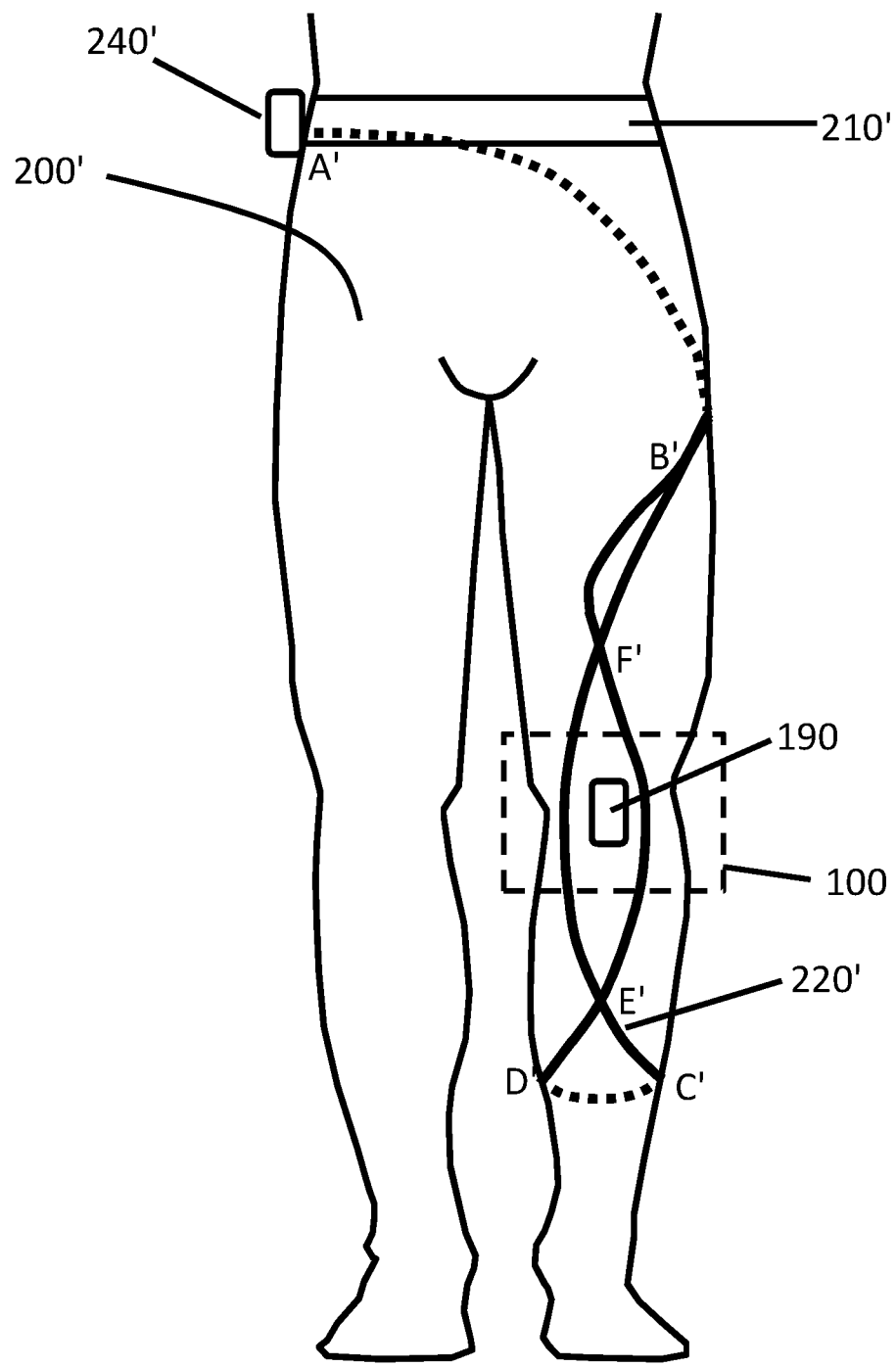
FIG. 3 is a drawing of another embodiment of a bracing garment for bracing the human left knee.

A second embodiment of a garment according to the present invention is shown in FIG. 3 as garment 200' with belt 210', tension member 220', and tensioner 240'. In this embodiment, the schematic path of tension member 220' starts at point A' at tensioner 240' on the right hip on belt 210'. It then proceeds from point A' around the back of the wearer (shown in a broken line) to point B', located on the lateral side of the left leg, where tension member 220' splits in its path to form a single closed loop. The loop proceeds from the left lateral side to pass patella 190 of the left leg on the medial side before curving around again to reach the lateral side of the left leg at point C' at the distal portion of the triceps surae, from where it proceeds around the back of the leg once more (shown in broken line) to the medial side of the left leg at point D'. It then proceeds from point D', to cross over its own path at point E', in order to proceed along a curved path around the lateral side of patella 190 before again crossing over its own path at point F'. The path then curves sharply to the left lateral side to arrive at the point B', where it rejoins itself. At crossover points E' and F' the outgoing and incoming portions of tension member 220 are independent, they do not join each other and are arranged to move as freely from each other as possible.

In this arrangement, tension member 220', by virtue of circling the leg, not only produces or exerts a stabilizing compressive force on knee region 100 but also produces or exerts forces on the leg and garment that allow the tension member to clamp the leg in region C'-D'-E' around the calf. Tension member 220' therefore serves as its own distal anchor to the leg and is anchored at the top in belt 210' and by the fact that tension member 220' completes at least a partial portion, perhaps a major portion, of a circle about the body. In operation, tension member 220' may have its tension adjusted by the wearer of garment 200' via tensioner 240'. In other embodiments, the tensioner may be located further around the anterior of the torso so that tension member 220' completes a circle around the thigh as seen from the top down along the leg. In this disclosure, the phrase "fully encircles the thigh" is used to describe this latter situation, even though the actual path may be in the nature of a spiral. The segment of tension member 220' extending from point A' to point B' in FIG. 3 may also be viewed as an anchor member, as it fulfills the same role as anchor member 230 in the embodiment of FIG. 2.

The embodiment of FIG. 3 specifically shows tension member 220' crossing over itself both above and below the knee. In a more general embodiment it needs only cross over itself either above or below the knee. However, there is merit in the downward and upward portions of the path of tension member 220' approaching each other on the side of the knee opposing that on which tension member 220' in fact does cross over itself.

Figure 4:
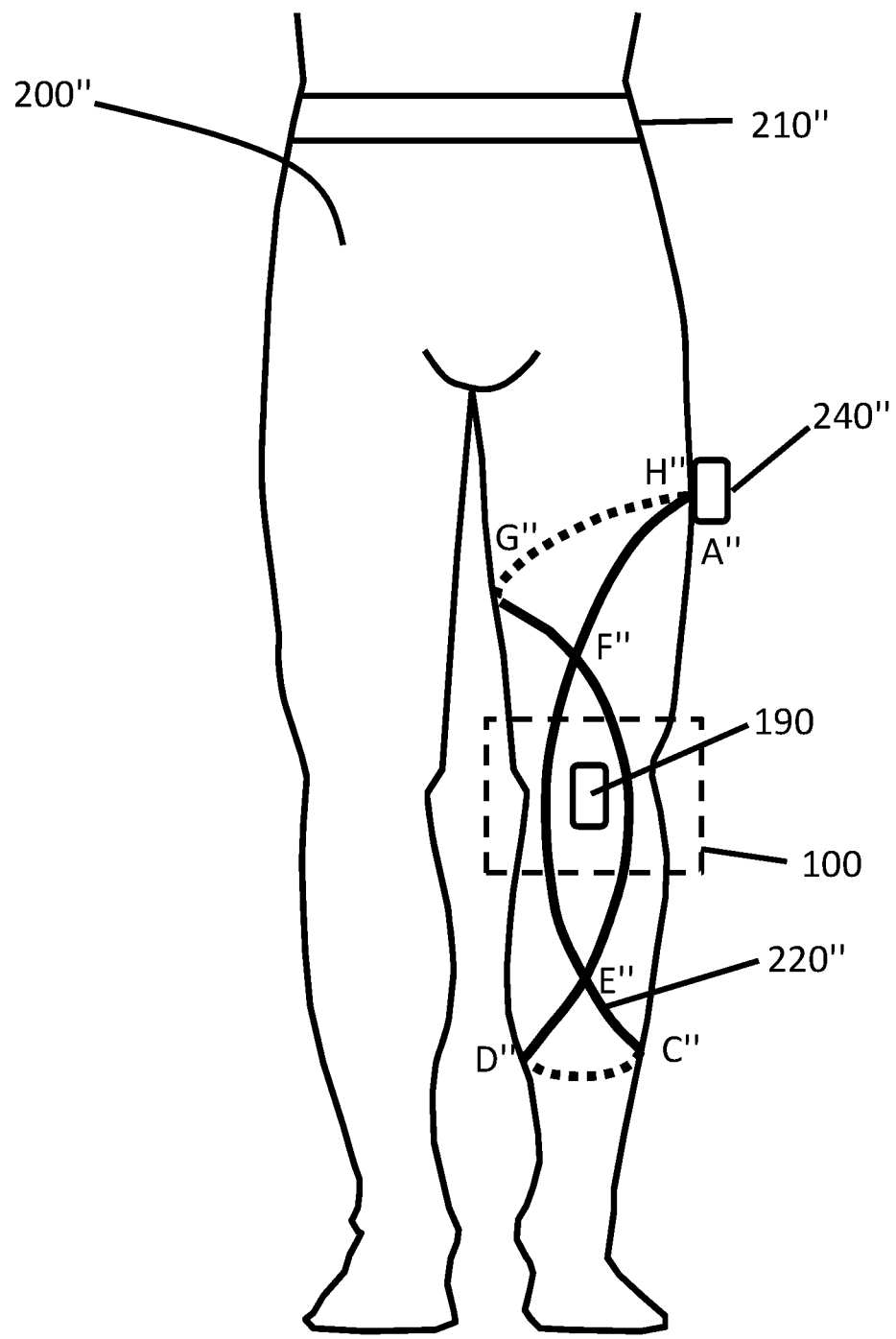
FIG. 4 is a drawing of another embodiment of a bracing garment for bracing the human left knee

A further embodiment of the garment is shown in FIG. 4 as garment 200" with belt 210", tension member 220", and tensioner 240". In this embodiment, the schematic path of tension member 220" starts at point A" at tensioner 240". It then proceeds from point A" to pass patella 190 of the left leg on the medial side before curving around again to reach the lateral side of the left leg at point C" at the distal portion of the triceps surae, from where it proceeds around the back of the leg (shown in broken line) to the medial side of the left leg at point D". It then proceeds from point D", to cross over its own path at point E", in order to proceed along a curved path around the lateral side of patella 190 before again crossing over its own path at point F". It curves around the medial side of the thigh at point G" and proceeds around the back of the thigh over the posterior of the thigh (shown in broken lines) to tensioner 240" at point H". At crossover points E" and F" the outgoing and incoming portions of tension member 220" do not join each other and are arranged to move as freely from each other as possible.

In this arrangement, tension member 220", by virtue of circling the leg, not only produces or exerts a stabilizing compressive force on knee region 100 but also produces or exerts forces on the leg and garment that allow the tension member to clamp the leg in region C"-D"-E" around the calf. Tension member 220" therefore serves as its own distal anchor to the leg. Similarly, by virtue of circling the leg about the thigh it anchors the garment to the thigh. In operation, the tension member may have its tension adjusted by the wearer of garment 200" via tensioner 240".

The embodiment of FIG. 4 specifically shows tension member 220" crossing over itself both above and below the knee. In a more general embodiment it needs only cross over itself either above or below the knee. However, there is merit in the downward and upward portions of the path of tension member 220'' approaching each other on the side of the knee opposing that on which tension member 220'' in fact does cross over itself.

In the embodiments of FIG. 2, FIG. 3 and FIG. 4, tension member 220, 220', 220'' in each case describes a tensionable loop, even if the tensionable loop is not circular and despite tensioner 240, 240', 240'' being in the loop in some cases. Furthermore, in the various embodiments, tension member 220, 220', 220'' and anchor member 230 separately or jointly either wholly, in major part, or at least partially encircle the thigh.

In the embodiments shown in FIG. 2 and FIG. 4, the garment need not assume the form of a complete lower body garment and need only cover the relevant portion of the leg being stabilized. The anchoring arrangements of FIG. 2 and FIG. 4 obviate belt 210, 210''. It is therefore possible for the embodiments shown in FIG. 2 and FIG. 4 to be implemented in the form of a hose for the affected leg, the hose extending from the upper thigh to below the calf. Wearers may prefer to employ a more extensive garment for aesthetic reasons. Even if it assumes the general aspect of a complete lower body garment, the self-anchoring aspect of tension member 220, 220'' makes it possible for the garment not to have to extend to or over the feet. Garment 200, 200', or 200'' may envelope the knee wholly, or only in part. For example, the posterior of the knee or the patella may in principle remain uncovered by garment 200, 200' or 200''.

The choice of the exact path of tension member 220, 220', 220'' is dictated by the forces required for stabilizing the knee, which in turn is dictated by the support and compression desired for the four ligaments in the knee discussed above at the hand of FIG. 1. In this respect it will be noted that tension member 220, 220', 220'' passes proximate the two lateral ligaments MCL and LCL to compress the knee in those areas. The path of tension member 220, 220', 220'' is therefore predetermined by the location of the ligaments. In FIG. 2, FIG. 3 and FIG. 4, a single tension member is employed disposed longitudinally along a predetermined path. That is, the tension is directed longitudinally along the path. The garment may in general comprise one or more tension members each disposed longitudinally along a corresponding predetermined curved three-dimensional spatial path within or on a matrix of a garment material, the corresponding predetermined paths spatially relating the one or more tension members to at least one natural ligament of the anatomical joint.

We turn now to the nature of tension member 220, 220', 220'' and its interaction with the matrix of the material from which garment 200, 200', 200'' is fashioned. FIG. 2, FIG. 3 and FIG. 4 schematically show the paths of tension members 220, 220', 220'', but not how tension member 220, 220', 220'' is housed or retained in or on garment 200, 200', 200''. Tension members 220, 220', 220'' have to be free to move within garment 200, 200', 200'' without crumpling or significantly distorting the garment. To achieve this, tension members 220, 220', 220'' are routed along their paths within conduits in the matrix of the material from which garment 200, 200', 200'' is fashioned. The conduits may comprise natural passages within the weave of the material of the garment. In other embodiments, the conduits may be tubular in nature and may be disposed within or external to but attached to the material matrix of garment 200, 200', 200''. In yet further embodiments, the conduits may comprise segments of tubing, also described in the present disclosure by the term "collated tubing". The use of collated tubing allows the degree of friction between tension member 220, 220', 220'' and the matrix material of garment 200, 200', 200'' to be modified. In yet further embodiments, the conduits may be fashioned from a clothing material different from that of the matrix of garment 200, 200', 200''. In yet further embodiments, the conduits may be fashioned by a stitching pattern that demarcates the tension member path either side of tension member 220, 220', 220''. A special case of such a stitched arrangement is one in which the material of the garments is stitched together in a seam, and tension member 220, 220', 220'' extends longitudinally within the seam.

Tension member 220, 220', 220'' may comprise a plurality of individual strands extending along individual conduits, the individual strands being joined together before entering tensioner 240, 240', 240''. Tension member 220, 220', 220'' may be formed of a material that is substantially less extensible than the material matrix of the garment. Materials suited for use in tension member 220, 220', 220'' may be longitudinally inextensible but flexible. Suitable materials for tension member 220, 220', 220'' include, but are not limited to, stainless steel; Nylon; Kevlar®; Teflon®; ultra high molecular weight polyethylene-based fiber such as Dyneema®; and various fibers with a diamond or basket weave including cotton, polyester and polypropylene, for example without limitation Technora®. (Kevlar is a registered trademark of E. I. DU PONT DE NEMOURS AND COMPANY CORPORATION DELAWARE Chestnut Run Plaza, 974 Centre Road WILMINGTON DELAWARE 19805; Teflon is a registered trademark of THE CHEMOURS COMPANY FC, LLC LIMITED LIABILITY COMPANY DELAWARE 1209 ORANGE STREET WILMINGTON DELAWARE 19801; Dyneema is a registered trademark of DSM IP Assets B.V. LIMITED LIABILITY COMPANY NETHERLANDS Het Overloon 1 HEERLEN NETHERLANDS NL6411 TE; and Technora is a registered trademark of TEIJIN KABUSHIKI KAISHA (TEIJIN LIMITED) CORPORATION JAPAN 6-7, MINAMIHOMMACHI 1-CHOME CHUO-KU, OSAKA JAPAN) The conduit may be formed of the same material as the matrix material of the garment and be lined internally with a conduit material of lesser friction coefficient with respect to the tension member material so as to allow the tension member 220, 220', 220'' to move as freely as possible. The conduit material may be in the form of a tube or a collated tube. There is no particular structural limitation on the cross-section of the tube. A collated tube is useful in that it allows a very low friction tube material to be selected even if it is inextensible, because the collation segments may move closer to one another without unduly crumpling the garment 200, 200', 200'' when tension member 220, 220', 220'' is put under tension. As shown in FIG. 2, FIG. 3, FIG. 4 and FIG. 5, tensioner 240, 240', 240'' may be viewed as variously in or on the loop formed by the tension member 220, 220', 220''.

Considering tension members 220, 220', 220'' as freely moving within their respective conduits, we now return to FIG. 2 in order to elucidate the matter of the relationship between anchor member 230 and tension member 220 at point I. To this end, the thigh region of FIG. 2 is shown enlarged and with more detail in FIG. 5. In one embodiment, anchor member 230 may extend from point G to point I along conduit 232 similar to conduit 222 of tension member 220. In order for this latter arrangement to function as an anchor, anchor member 230 is attached to end 234 of conduit 232 proximate point I. It is to be noted that anchor member 230 is not attached to tension member 220 at point I, because tension member 220 needs to remain free to move within conduit 222. In this arrangement, the portion of tension member 220 extending from point A at tensioner 240 to point I, together with the whole of anchor member 230 form an anchor that extends around the thigh. As tension member 220 needs to be able to move freely past point I, the curvature of the path of tension member 220 at point I has an upper curvature limit dictated by the flexibility of tension member 220. This favors a materials choice for tension member 220 that requires the material to be substantially longitudinally inextensible, yet highly flexible. This makes a variety of fibers with a diamond or basket weave including cotton, polyester and polypropylene useful for the particular embodiment in FIG. 2 and FIG. 5.

Figure 5:
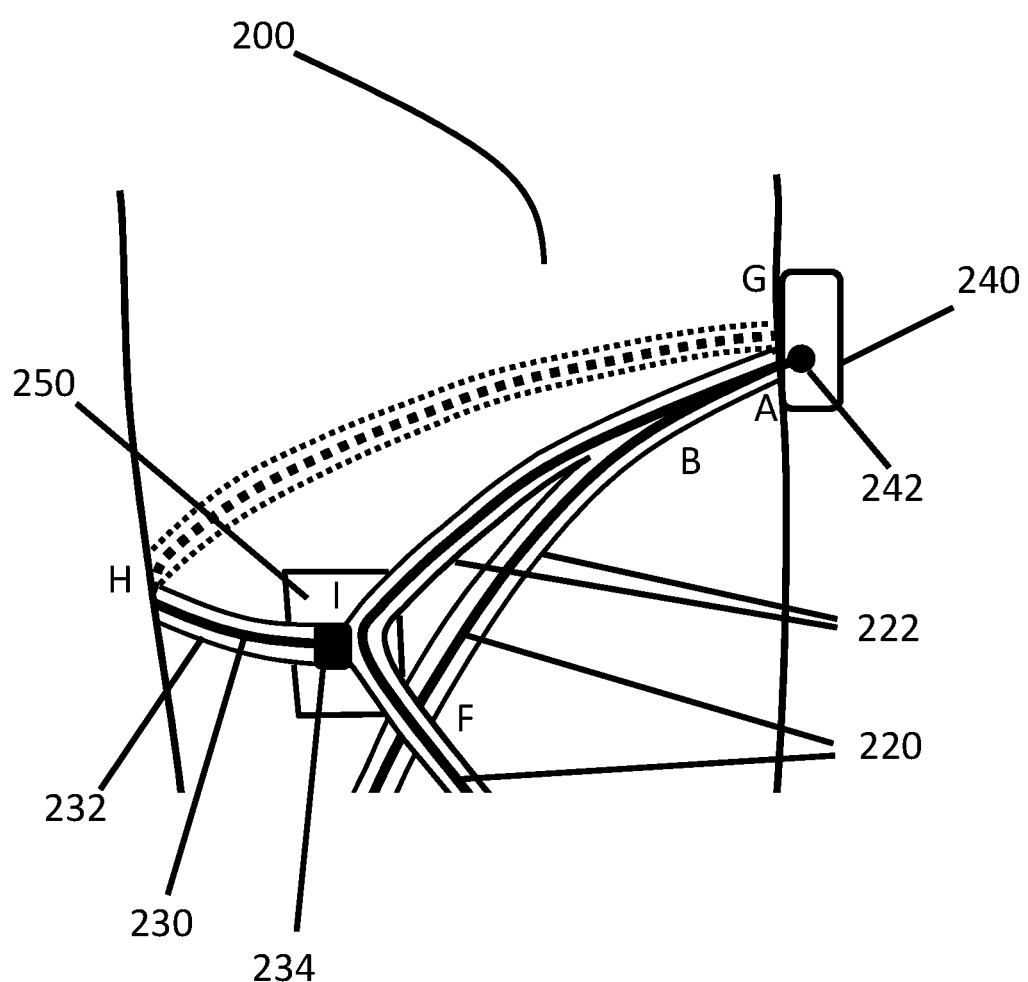
FIG. 5 shows the thigh portion of FIG. 2 enlarged and with more detail.

Any portion 250 of garment 200 between anchor member 230 and tension member 220 may be made from inextensible material to ensure that any tension applied to anchor member 230 by tensioner 240 does not simply stretch portion 250 of garment 200 proximate the region between anchor member 230 and tension member 220. In other embodiments, the end of anchor member 230 near point I may be shaped into a loop in order to spread the force acting at the end of anchor member 230 over a larger area to avoid pulling or deforming the fabric of garment 200. FIG. 5 also shows tension member 220 entering tensioner 240 via tensioner port 242.

There is much freedom in the choice of the matrix material or fabric of the garment 200, 200', 200". There is some merit in using a material with considerable elasticity, for example without limitation Spandex or mixes of Spandex with other fibers, including for example without limitation cotton. This allows the garment to be made with an intentionally tight fit. This reduces the possibility of crumpling when tension member 220, 220', 220" is put under tension.

Figure 6A:
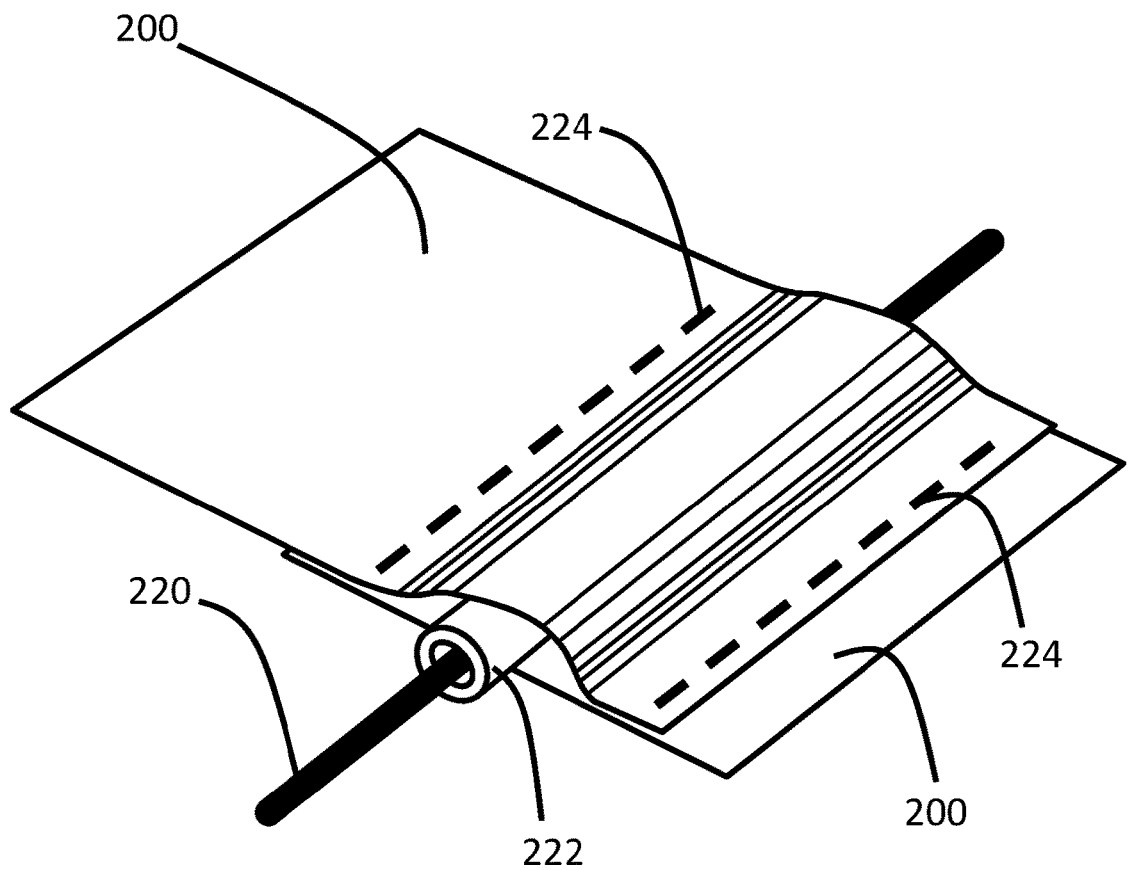
FIG. 6A shows an arrangement of a tension member and conduit in one embodiment
Figure 6B:
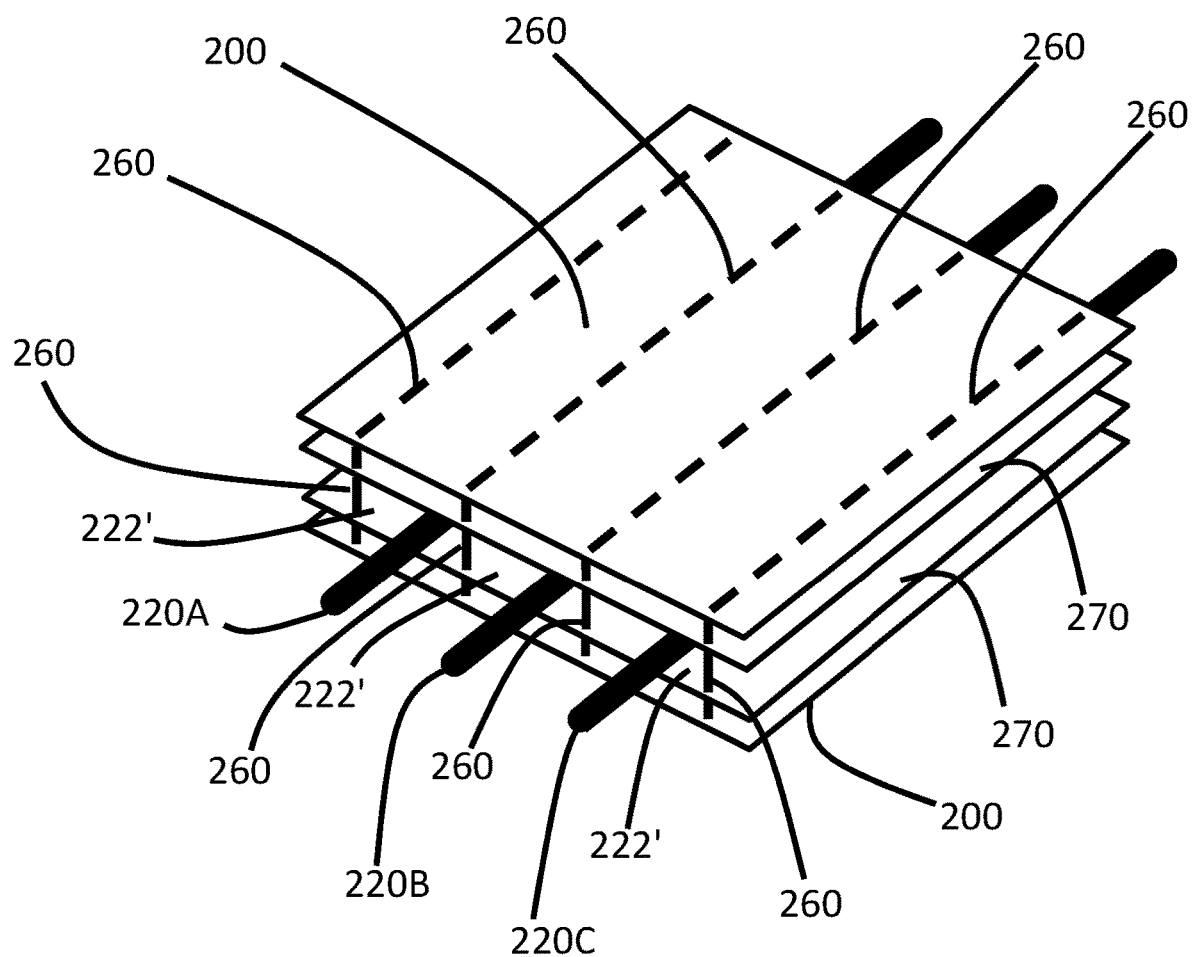
FIG. 6B shows an arrangement of tension members and conduits in another embodiment.
Figure 6C:
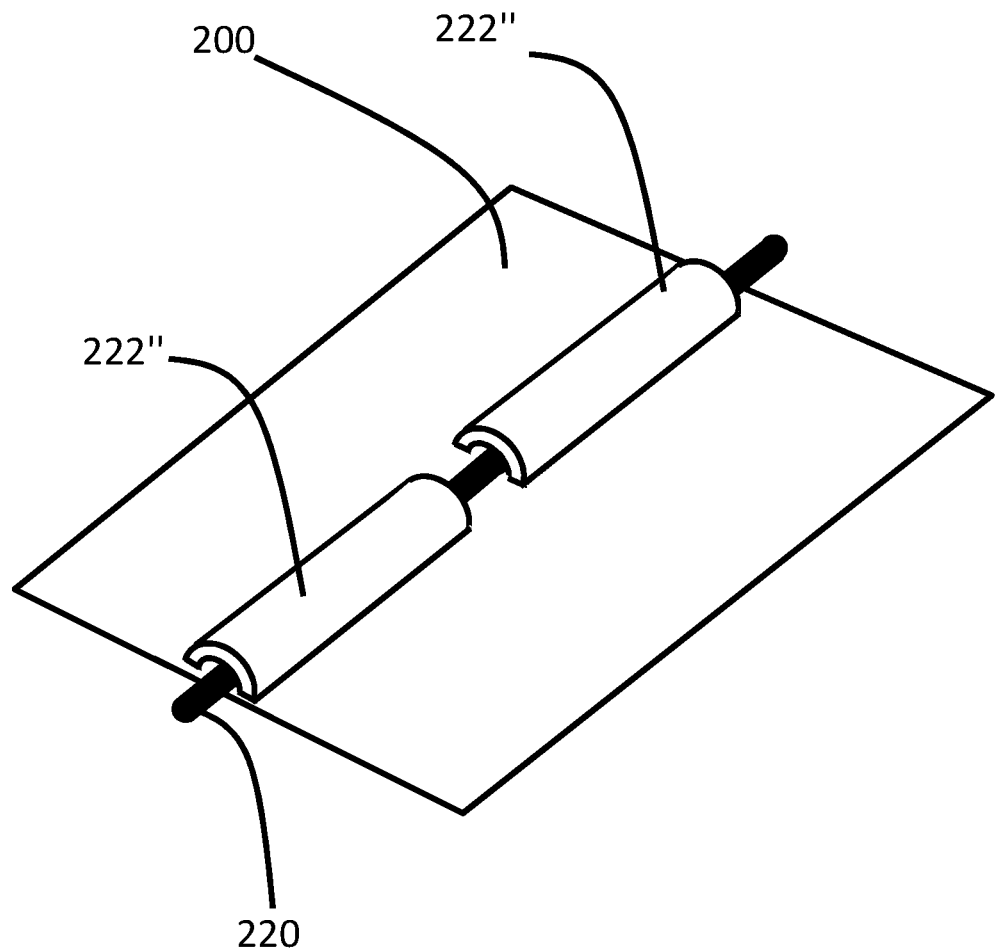
FIG. 6C shows an arrangement of a tension member and conduit in another embodiment.
Figure 7:
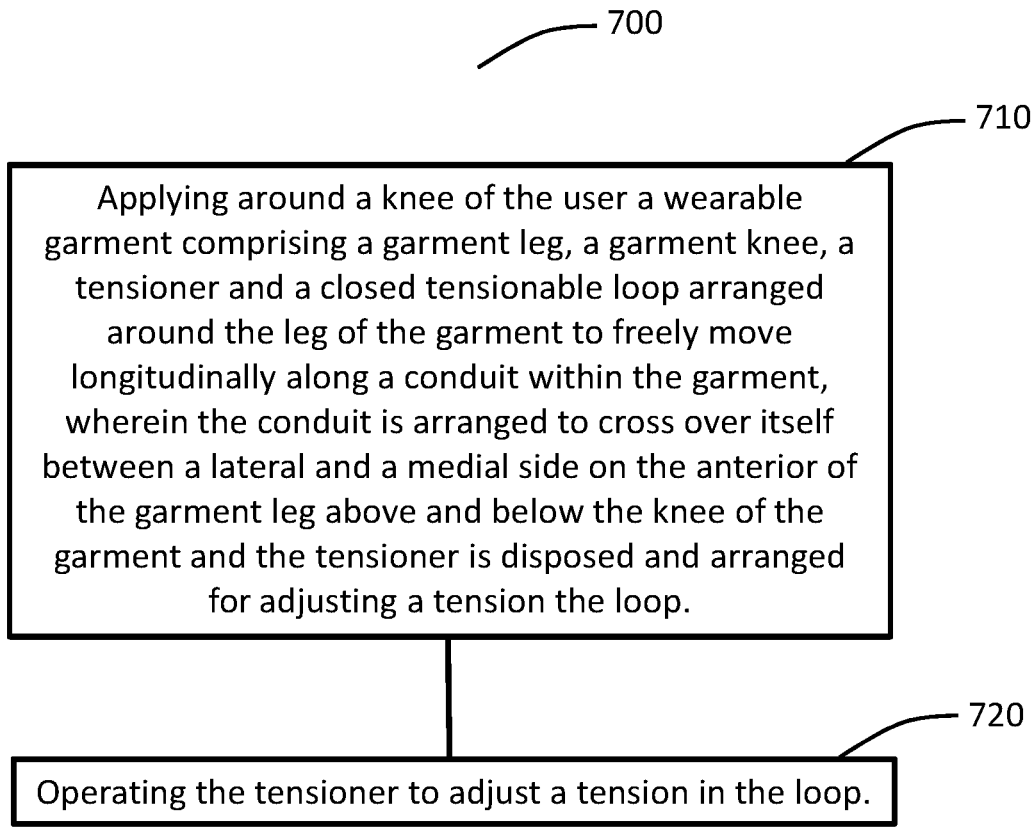
FIG. 7 is a flow chart diagram of a method for stabilizing a knee of a human leg.

FIG. 6A, FIG. 6B, and FIG. 6C show different implementations of conduits for use with tension members. Using the elements of FIG. 2 and FIG. 5 as example, FIG. 6A shows a seam in garment 200 material matrix created by stitches 224, with conduit 222 extending along the seam in the form of tube in this embodiment. Tension member 220 extends longitudinally through conduit 222. The material of conduit 222 is selected to have a low coefficient of friction with tension member 220. In a more general case, there may be a plurality of seams, each having conduit 222 extending longitudinally along it and each conduit 222 having a strand of tension member 220 extending longitudinally along it. In FIG. 6A, conduit 222 is shown as circular in cross-section, but in other embodiments it may have any suitable cross-section that allows the strand of tension member 220 to move substantially freely, while simultaneously making conduit 222 compatible with the ergonomic requirements to which the garment is subject. One suitable cross-section is semi-circular, or a smaller segment of a circle with enough curvature to accommodate the strand of tension member 220, while being flat on one side so as to be easily integrated in garments material 200. It has already been explained that conduit 222 may be collated, which allows very low friction, but inextensible tubing to be employed. Example materials for the tubing include, but are not limited to Teflon® and silica. In a related embodiment, the strand of tension member 220 is simply sandwiched between two strips of low fiction material inside a stitched seam. In a further embodiment, seams may be created by joining adjacent material matrices by an adhesive, heat sealing, or other conjoining mechanism, and a conduit formed between suitable spaced-apart seams. Conduits may be similarly implemented in the embodiments of FIG. 3 and FIG. 4.

FIG. 6B shows another embodiment of a way to incorporate tension member 220 within the matrix material of garment 200. The drawing is an edge-on view of the weave of garment 200. It shows four rows 260 of stitching or weave either side of every one of three strands of tension member 220 within the matrix material of garment 200. The three strands of tension member 220, being 220A, 220B, and 220C, are sandwiched between two longitudinal strips 270 of low friction material held by stitching 260. In this drawing, the material of garment 200 is shown as being two sheets. This should be considered as presented schematically for the sake of clarity, as the material is in practice woven. The fiber of the stitching may be a low friction material so that tension member 220 slides on all sides against low friction material. In this embodiment, conduits 222' are formed by low friction material strips 270 and low friction material stitching 260. This embodiment may be implemented at seams in garment 200 or the sandwiching of garment material 200 with low friction material 270 may be implemented over the entire area of tension member 220. The conduits may be similarly implemented in the embodiments of FIG. 3 and FIG. 4.

FIG. 6C shows an embodiment in which conduit 222" is attached to the surface of garment 200 in the form of collated semi-cylindrical tubes and tension member 220 routed through conduit 222". In some embodiments, the bases of the tubes may be closed or may be lined with a low friction material. In FIG. 6A, FIG. 6B, and FIG. 6C tension member 220, 220', 220" is shown as circular in profile or cross-section. In a general embodiment, there is no limitation on the profile or cross-section of the tension member 220, 220', 220".

In a further aspect, method [700] is presented for stabilizing a knee of a human user leg, comprising: applying [710] around a knee of the user wearable garment 200, 200', 200" comprising a garment leg, a garment knee, tensioner 240, 240', 240" and closed tensionable loop 220, 220', 220" arranged around the leg of garment 220, 220', 220" to freely move longitudinally along conduit 222, 222', 222" within or on garment 200, 200', 200", wherein conduit 222, 222', 222" is arranged to cross over itself between a lateral and a medial side on the anterior of the garment leg at least one of above (point F, F', F") and below (point E, E', E") the knee of garment 200, 200', 200" and tensioner 240, 240', 240" is disposed and arranged for adjusting tension of loop 220, 220', 220"; and operating [720] tensioner 240, 240', 240" to adjust tension in loop 220, 220', 220". In some embodiments garment 200, 200', 200" may be applied such that conduit 222, 222', 222" is arranged to cross over itself between a lateral and a medial side on the anterior of the garment leg both above (point F, F', F") and below (point E, E', E") the knee of garment 200, 200', 200".

Applying [710] may comprise: arranging garment 200, 200', 200" on the user to position a first portion of loop (C, C', C" to D, D', D") against a distal region of a triceps surae of the user leg; positioning a second portion of the loop (the portion at above point F, F', F") on or above a thigh of the user leg; and positioning on the medial and lateral sides of a patella of the user leg proximate two collateral ligaments of the user knee third and fourth portions of the loop located on the loop between the first and second portions (both between E, E', E" and F, F', F"). The positioning of the second portion of the loop may comprise positioning the second portion of the loop against the posterior of the thigh of the user leg (see FIG. 4).

Figure 8:
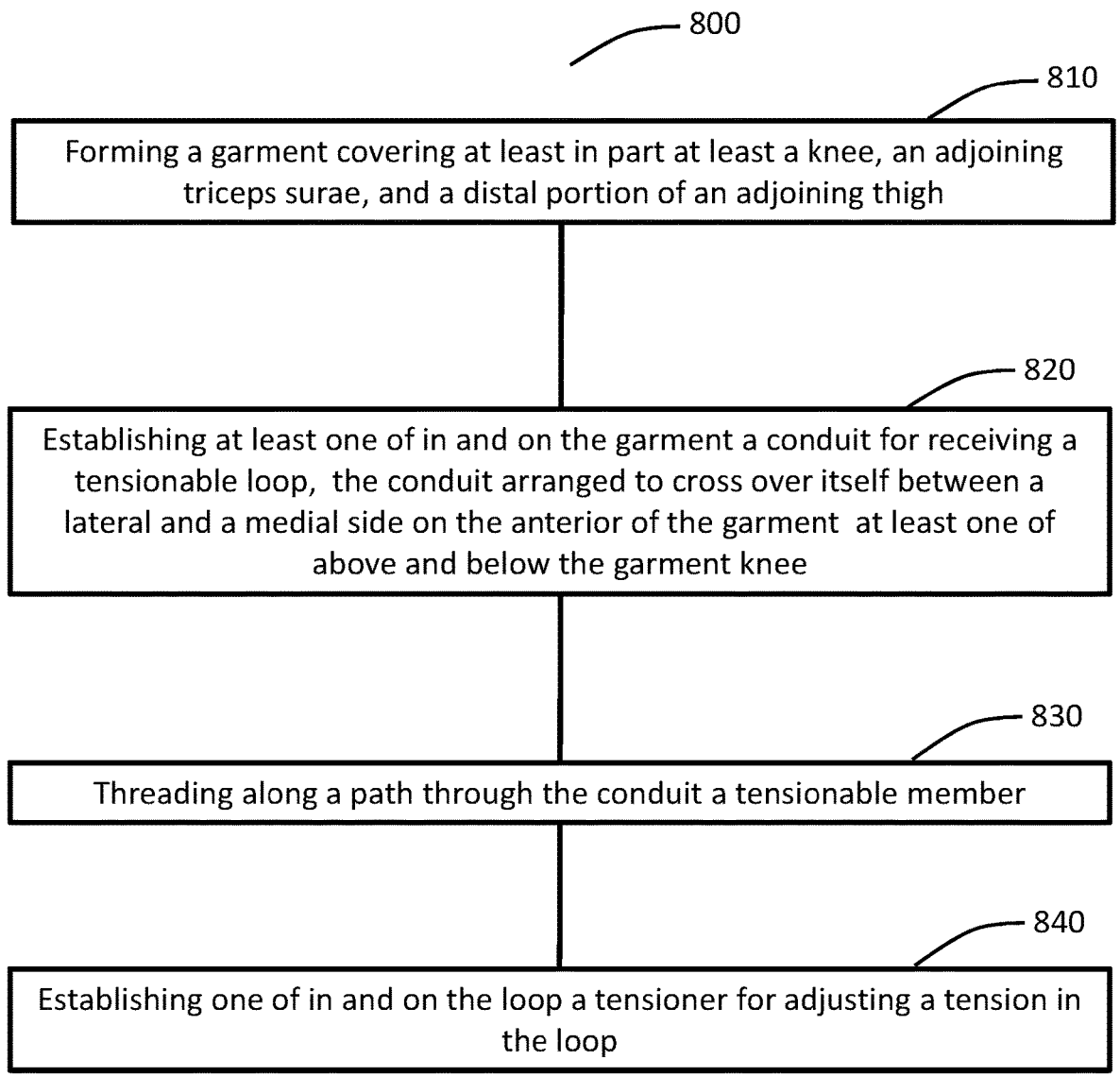
FIG. 8 is a flow chart diagram of a method of manufacturing a bracing garment for bracing the human knee.

In a further aspect, described at the hand of the flow chart of FIG. 8, method [800] is presented for manufacturing a wearable garment for stabilizing a knee of a user, the method comprising: forming [810] a garment covering at least in part at least a knee, an adjoining triceps surae, and a distal portion of an adjoining thigh; establishing [820] at least one of in and on the garment a conduit for receiving a tensionable loop, the conduit arranged to cross over itself between a lateral and a medial side on the anterior of the garment at least one of above and below the garment knee; threading [830] along a path through the conduit a tensionable member; establishing [840] one of in and on the loop a tensioner for adjusting a tension the loop.

Threading [830] the tensionable member may comprise threading a tensionable member that is substantially inextensible. Threading [830] the tensionable member may comprise threading a tensionable member that is flexible and substantially inextensible. Threading [830] the tensionable member may comprise threading a tensionable member made from one or more of PTFE, stainless steel, Nylon; Kevlar®; one or more ultra high molecular weight polyethylene based fiber, a fiber with a diamond weave. Threading a tensionable member made from the fiber with a diamond weave may comprise threading a tensionable member made from one of cotton, polyester, polypropylene, and Technora®.

Establishing the conduit [840] may comprise arranging the conduit to cross over itself above and below the knee. Forming the garment [810] may comprise extending the garment to a waist of the user, forming a belt around the waist. Establishing the tensioner may comprise establishing the tensioner on the belt. Establishing [840] the tensioner in or on the loop may comprise establishing the tensioner on a thigh of the garment.

Figure 9:
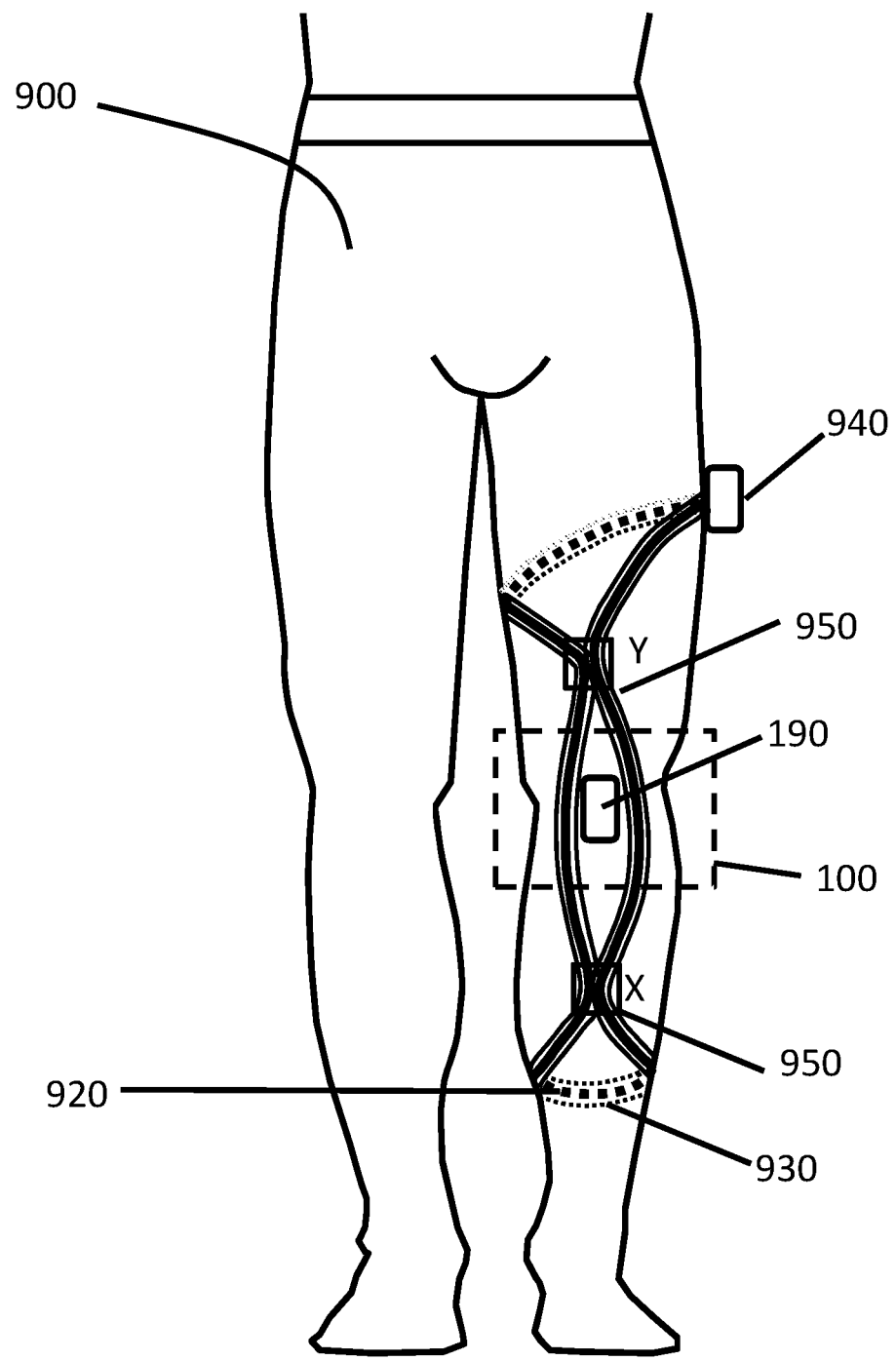
FIG. 9 is a drawing of a further embodiment of a bracing garment for bracing the human left knee.

In a further embodiment, shown in FIG. 9, a wearable garment 900 is presented for stabilizing knee 100 of a user comprising: closed tensionable loop 920 arranged to freely move along conduit 930 disposed within or on garment 900, conduit 930 extending along a conduit path having relative to knee 100 a lateral portion and a medial portion; and adjustable tensioner 940 in or on loop 920 for adjusting a tension in loop 920, wherein the lateral and medial portions of the conduit path pass patella 190 of user knee 100 proximate lateral 170 and medial 180 collateral ligaments of user knee 100 in FIG. 1 respectively and in which the lateral and medial portions of the conduit path closely approach each other at one or more than one point, the at least one point being at least one of below (point X) and above (point Y) user knee 100. Broken lines in FIG. 9 indicate that the conduit and tensionable loop are on the posterior of the leg.

The lateral and medial portions of the conduit path may closely approach each other at both a first point (point X) below user knee 100 and at a second point (point Y) above user knee 100. It should be noted that, while the actual conduits portions may overlap at point X and point Y, the lateral and medial portions of the tensionable loop inside the conduit are not joined at point Y or point X. Tensionable loop 920 may be disposed for applying pressure to at least one of lateral collateral ligament 170 and medial collateral ligament 180 of the user when garment 900 is worn by the user and the tensionable loop is tensioned by operating tensioner 940. Conduit 930 may be arranged along a path that substantially circles the leg at a distal region of the triceps surae of the leg, as shown in FIG. 9. This anchors garment 900 to the triceps surae. Tensionable loop 920 may comprise a tension member extending along conduit 930. Tensioner 940 may be disposed on the thigh of the user. The tension member may be made of a substantially longitudinally inextensible material and the material may be flexible. Loop 920 may be arranged in or on the material of garment 900 in the same way as shown in FIG. 6A, FIG. 6B and FIG. 6C and in the text accompanying those drawings. Conduit 930 may comprise a low friction tube and the tube may be collated. As with the embodiment of FIG. 4, the tensionable loop 920 in FIG. 9 extends substantially around the thigh, thereby anchoring garment 900 to the thigh.

The anchoring arrangements on the thigh of the user employed in the embodiments shown in FIG. 2, FIG. 3, and FIG. 4 may also be applied to the embodiment in FIG. 9. In order to ensure that the material of garment 900 does not deform and stretch and thereby disrupt the forces applied by the tensionable loop 920, portions 950 of the garment may be made from suitable inextensible materials. The embodiment of FIG. 9 may be viewed as a very similar to the case of FIG. 4, but without loop 920 overlapping itself.

Figure 10:
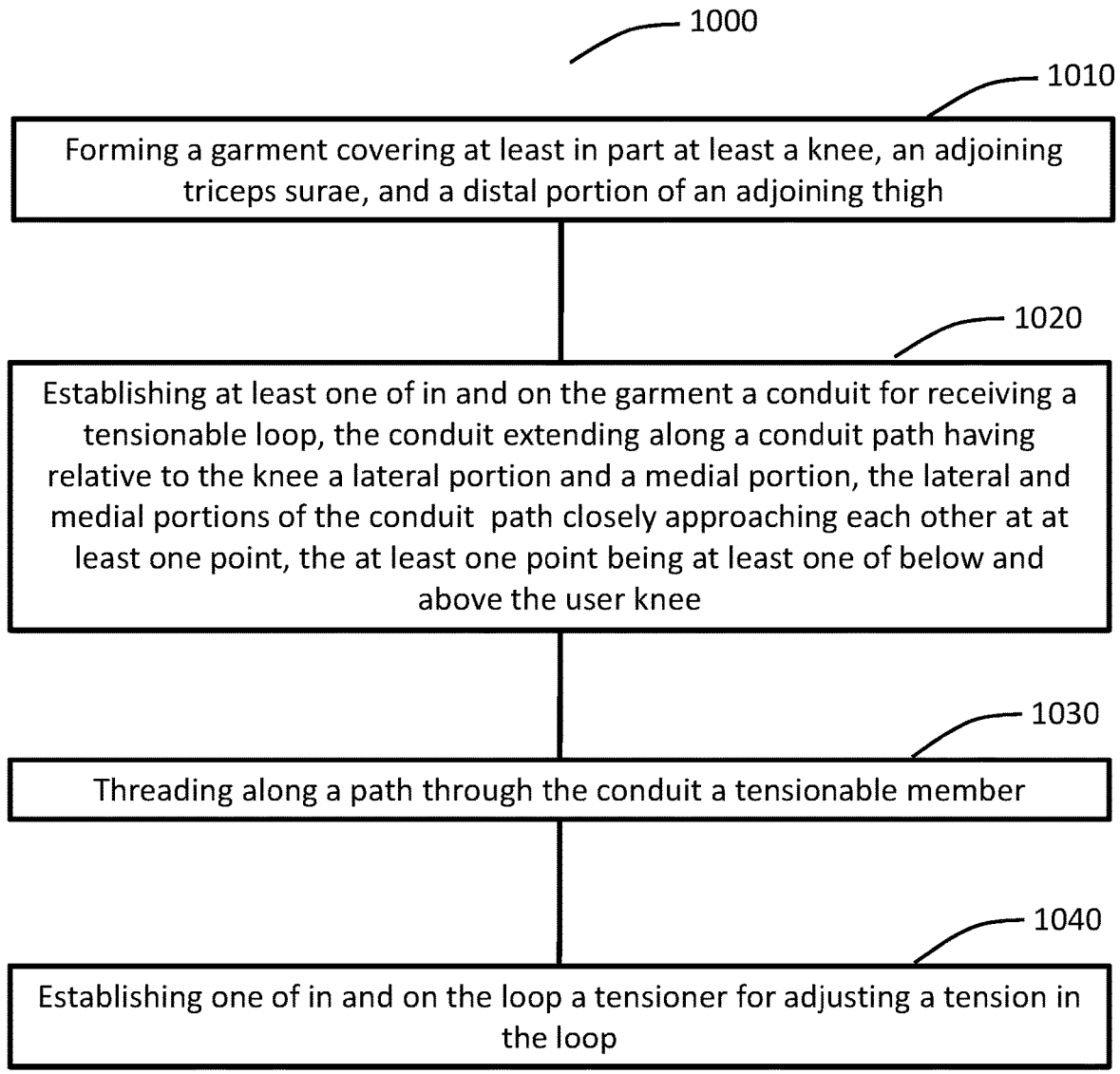
FIG. 10 is a flow chart diagram of another method of manufacturing a bracing garment for bracing the human knee.

In a further aspect, described at the hand of FIG. 10, method [1000] is presented for manufacturing wearable garment 900 for stabilizing a knee 100 of a user, the method comprising: forming [1010] garment 900 covering at least in part at least knee 100, an adjoining triceps surae, and a distal portion of an adjoining thigh; establishing [1020] at least one of in and on the garment conduit 930 for receiving tensionable loop 920, conduit 930 extending along a conduit path having relative to knee 100 a lateral portion and a medial portion, the lateral and medial portions of the conduit path closely approaching each other at least one point, the at least one point being at least one of below and above the user knee 100; threading [1030] along a path through conduit 930 a tensionable member; establishing [1040] one of in and on the loop tensioner 940 for adjusting a tension in loop 920.

Threading [1030] the tensionable member may comprise threading a tensionable member that is substantially inextensible. Threading [1030] the tensionable member may comprise threading a tensionable member that is flexible and substantially inextensible. Threading [1030] the tensionable member may comprise threading a tensionable member made from one or more of PTFE, stainless steel, Nylon Kevlar®; one or more ultra high molecular weight polyethylene based fiber, a fiber with a diamond weave. Threading a tensionable member made from the fiber with a diamond weave may comprise threading a tensionable member made from one of cotton, polyester, polypropylene, and Technora®. Establishing [1020] conduit 930 may comprise arranging conduit 930 to have the lateral and medial portions of the conduit path closely approaching each other both below and above user knee 100. Forming [1010] garment 900 may comprise extending garment 900 to a waist of the user, forming a belt around the waist, in which establishing tensioner 940 comprises establishing tensioner 940 on the belt. Establishing [1040] tensioner 940 in or on the loop may comprise establishing the tensioner on a thigh of the garment.

In a variant of the embodiment of FIG. 4, a portion of tension member 220" may comprise a length of substantially longitudinally inextensible fabric incorporated within the fabric of garment 200". In FIG. 4, the relevant portion of tension member 220" composed of substantially longitudinally inextensible material may be, for example, segment G" to H". The remaining portion of tension member 220" may comprise of inextensible strands within conduits as already described above. The inextensible strands are anchored to the segment G"-H" at both of its ends. Tensioner 220" may be mounted on or at one end of the segment G"-H". In this variant of the embodiment in FIG. 4, tensioner 220" is mounted at end H″ of segment G″-H″ of substantially longitudinally inextensible material. In the same manner, portions of the tension members 220, 220′, 920 of the embodiments of FIG. 2, FIG. 3 and FIG. 9 may be comprised of substantially longitudinally inextensible material.

In the present specification, the term "substantially inextensible fabric" is used to describe a fabric extending in two dimensions that is substantially inextensible in at least a first direction. The fabric may or may not have a restriction on extensibility in a direction perpendicular to the first direction. Non-limiting examples of such materials include but are not limited to so-called 2-way-stretch fabrics with blends of materials including Spandex, Nylon, Dyneema®, Kevlar®, polyester, Ingeo®, olefin fibre, Lyocell, and/or cotton which are woven, knitted, or braided in such a fashion to allow stretch in required dimensions. (Ingeo is a registered trademark of NATUREWORKS LLC LIMITED LIABILITY COMPANY DELAWARE 15305 MINNETONKA BLVD MINNETONKA MINNESOTA 55345) The "2-way" stretching refers here to stretching in two opposing directions in a first dimension whilst remaining substantially inextensible in any direction perpendicular to the first direction. Other "substantially inextensible fabrics", including for example without limitation materials comprising Dyneema® fibers in a two-dimensional mesh embedded in a second fabric or in a sandwich structure, may have substantially no extensibility in any direction. The inextensibility is deemed "substantial" in comparison with the inextensibility of the matrix material of the fabric of garment 200″, the garment fabric being stretchable or extensible in comparison with the "substantially inextensible fabric".

Figure 11:
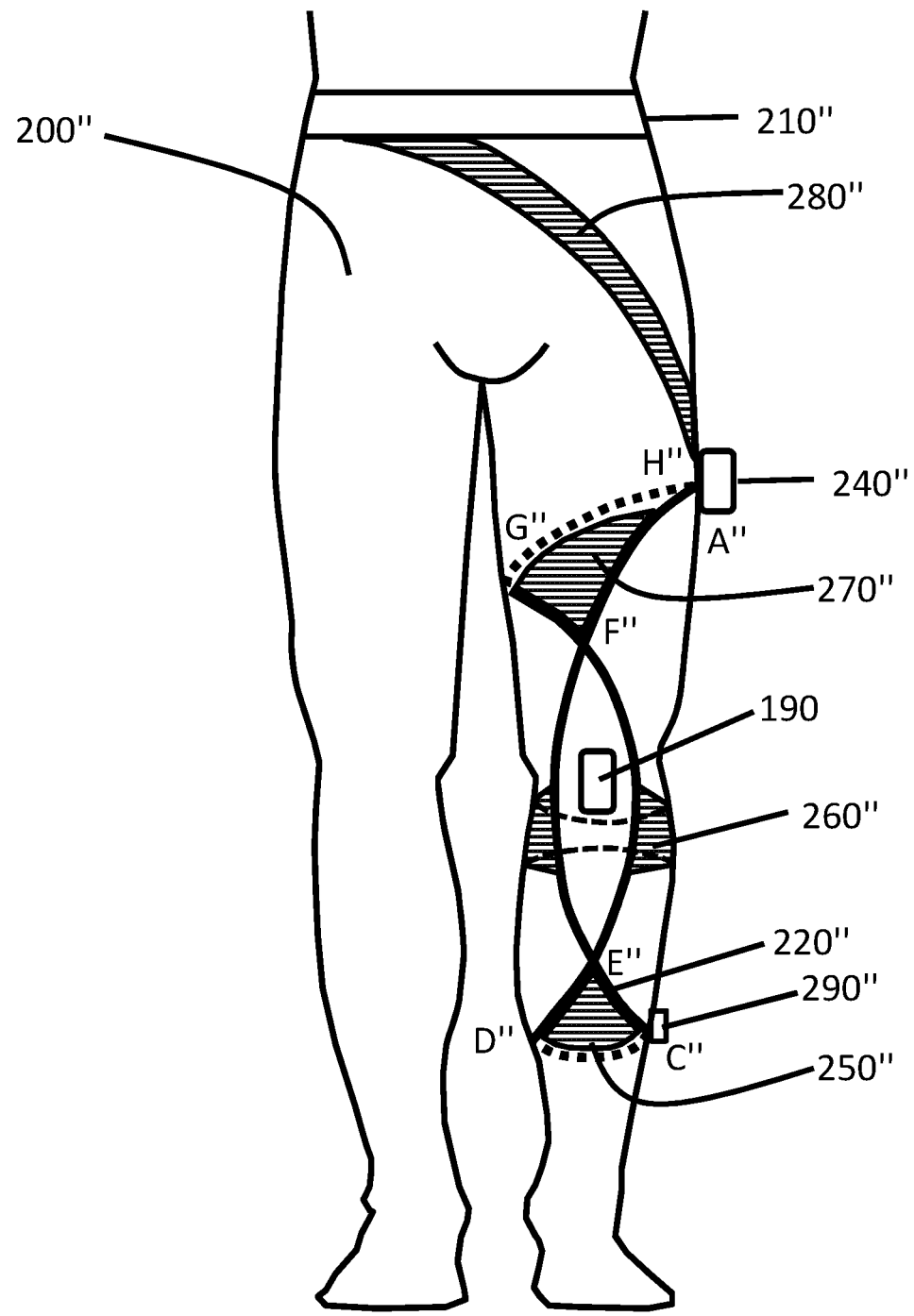
FIG. 11 is a drawing of another embodiment of a bracing garment for bracing the human left knee.

A further aspect of the wearable garment for stabilizing knee 100 of the user may be best described at the hand of FIG. 11, in which a variant of the garment of FIG. 4 is shown. The numbering of FIG. 4 is maintained in FIG. 11. Stabilizing connector 280″ connecting tension member 220″ to belt 210″ serves to keep garment 200″ from being pulled down as the tension in tension member 220″ is adjusted. Stabilizing connector 280″ may be implemented in many different ways, all of the implementations sharing the principle of connecting tension member 220″ to belt 210″. In FIG. 11 stabilizing connector 280″ is implemented as a belt of substantially inextensible fabric exhibiting inextensibility in at least the longitudinal direction in order to maintain tension in that direction. In FIG. 11, stabilizing connector 280″ is shown as extending across the front of garment 200″, but it may also extend simultaneously from tension member 220″ to belt 210″ across the rear of garment 200″. In other embodiments, stabilizing connector 280″ may comprise a substantially inextensible tensionable member disposed within a conduit and may therefore be of the same construction as tension member 220″.

In order to help ensure that garment 200″ is not unduly deformed or crumpled when the tension in tension member 220″ is adjusted, stabilizing portions 250″, 260″, and or 270″ of substantially inextensible fabric are incorporated in the fabric or matrix material of garment 200″ and attached to conduit 222 (see FIGS. 6A, 6B and 6C) of tension member 220″ or to the garment material or fabric immediately adjacent to conduit 222. The substantially inextensible fabric used for stabilizing portions 250″, 260″, and or 270″ is employed with at least the horizontal selected to be the inextensible direction.

Stabilizing portion 250″ on the anterior of the leg below and proximate crossover point E″ exerts on segments E″-C″ and E″-D″ of tension member 220″ forces with major components perpendicular to the paths of tension member 220″ along those two segments E″-C″ and E″-D″. Stabilizing portion 250″ may be fastened to the conduit bearing tension member 220″ along those two segments E″-C″ and E″-D″. In FIG. 11, stabilizing portion 250″ is shown as extending in a generally triangular shape over most of the anterior of the leg below crossover point E″ between segments E″-C″ and E″-D″. In general, stabilizing portion 250″ may extend over any fraction of the anterior of the leg below crossover point E″ between segments E″-C″ and E″-D″ in order to establish a lateral tension below crossover point E″ between segments E″-C″ and E″-D″ over the anterior of the leg.

Stabilizing portion 270″ may be disposed on the anterior of the leg above and proximate crossover point F″ and exerts on segments F″-A″ and F″-G″ of tension member 220″ forces with major components perpendicular to the paths of tension member 220″ along those two segments F″-A″ and F″-G″. Stabilizing portion 270″ may be fastened to the conduit bearing tension member 220″ along those two segments F″-A″ and F″-G″. In FIG. 11, stabilizing portion 270″ is shown as extending in a generally triangular shape over most of the anterior of the leg above crossover point F″ between segments F″-A″ and F″-G″. In general, stabilizing portion 270″ may extend over any fraction of the anterior of the leg above crossover point F″ between segments F″-A″ and F″-G″ in order to establish a lateral tension above crossover point F″ between segments F″-A″ and F″-G″ over the anterior of the leg.

Stabilizing portion 260″ over largely the posterior of the leg above and proximate crossover point F″ exerts on the medial and lateral segments E″-F″ of tension member 220″ forces with major components perpendicular to the paths of tension member 220″ along those lateral and medial segments E″-F″. Stabilizing portion 260″ may be fastened to the conduit bearing tension member 220″ along those lateral and medial segments E″-F″. In FIG. 11, stabilizing portion 260″ is shown as specifically extending in a generally rectangular shape over a portion of the posterior of the leg above crossover point E″ and below patella 190 between the lateral and medial segments E″-F″. In general, stabilizing portion 260″ may extend over any portion of the posterior of the leg below crossover point F″ and above crossover point E″ between lateral and medial segments E″-F″ in order to establish a lateral tension below crossover point F″ and above crossover point E″ between lateral and medial segments E″-F″ over the posterior of the leg. Consideration of the need for freedom of articulation of the knee may restrict the region between crossover points E″ and F″ that is covered by stabilizing portion 260″, leading to the example arrangement shown in FIG. 11.

In a general embodiment, stabilizing portions 250″, 260″, and or 270″ are comprised of fabric that is substantially inextensible in a generally horizontal direction and stabilizing portions 250″, 260″, and or 270″ are disposed to extend between horizontally opposing medial and lateral portions of tension member 220″, the lateral and medial portions of tension member 220″ exhibiting lateral tension with respect to each other in the garment when tension member 220″ is placed under longitudinal tension by operating tensioner 240″. As may be understood from FIG. 11, the lateral tension is induced around the posterior of the leg between crossover points E″ and F″ in the general area of patella 190, while below and above crossover points E″ and F″ the lateral tension is induced over the anterior of the leg. In the general case, garment 200″ may comprise a portion of inextensible fabric laterally joining two segments of tension member 220″ in tension with respect to each other horizontally over the leg.

Figure 12:
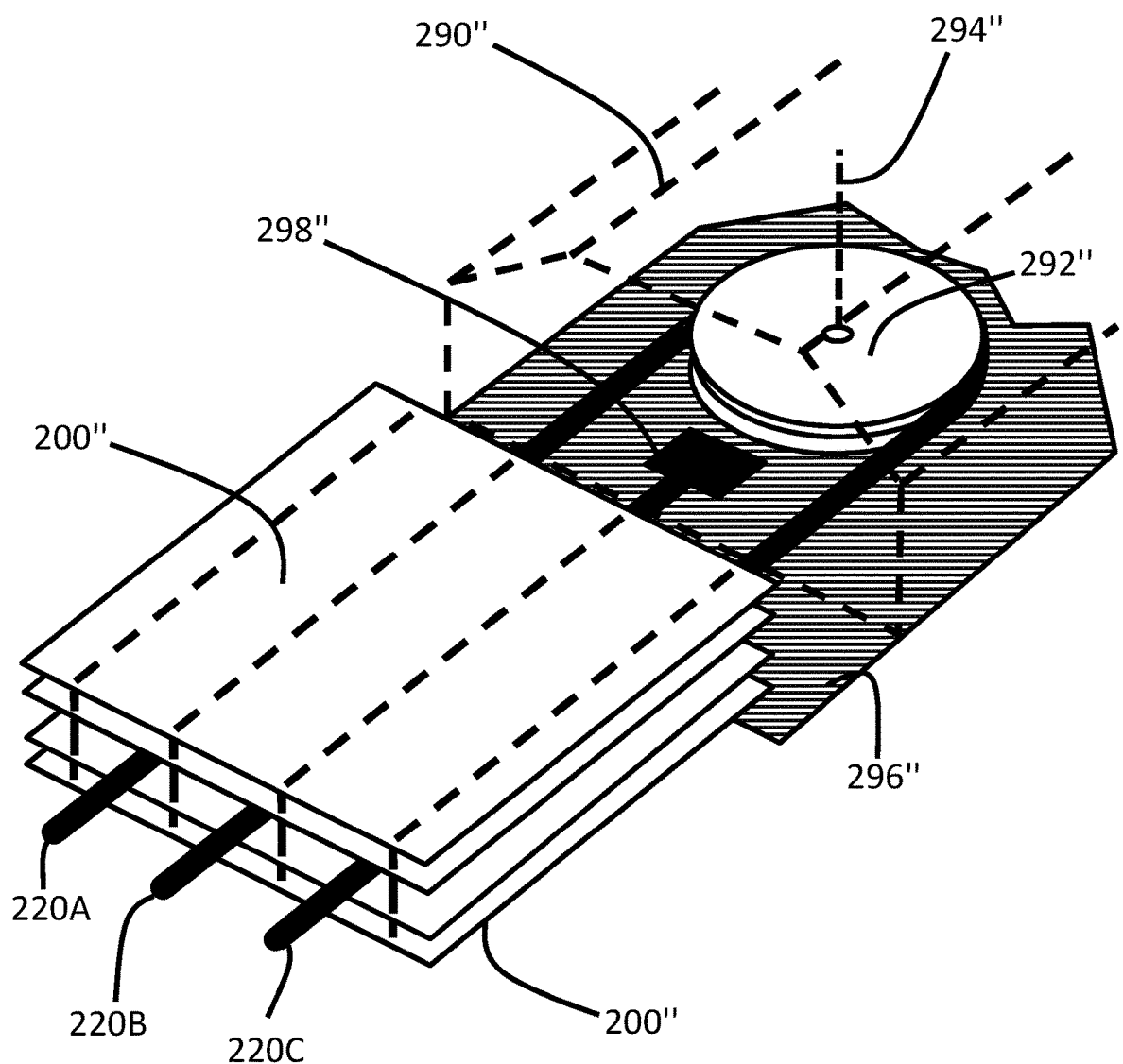
FIG. 12 is a drawing showing an embodiment of a tension regulator for use with the tension member of FIG. 6B.

In a further aspect, described at the hand of FIG. 12 with reference to FIG. 11 and FIG. 6B, garment 200" may comprise tension regulator 290" to balance the tension between at least two strands within tension member 220". By way of example we may consider tension member 220" as comprising of a plurality of strands 220A, 220B, and 220C as in FIG. 6B. In FIG. 12 we show one end of tension member 220", and thereby one end of strands 220A, 220B, and 220C. By way of non-limiting example, the end of tension member 220" shown in FIG. 12 may be proximate tension regulator 290" (see FIG. 11) disposed at the distal end of tension member 220". When the garment is worn by the user and the legs move, tension member 220" flexes and, in the absence of regulator 290", may lead to significant differences in tension in different strands of tension member 220". The presence of regulator 290" allows tension member 220" to flex without inducing unbalanced tensions that might disturb the functioning of garment 200" and the comfort of the user by warping tension member 220".

Figure 13:
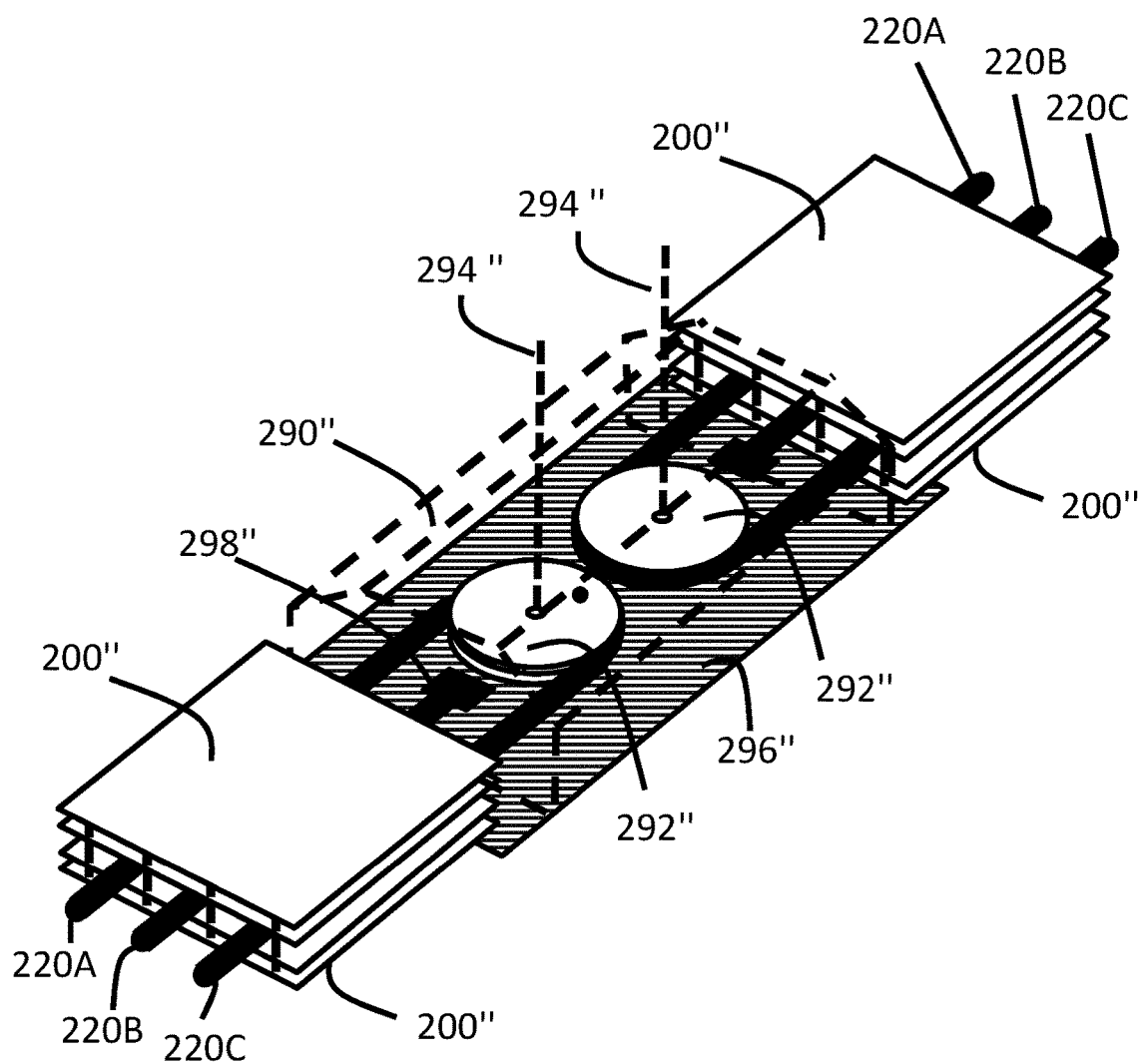
FIG. 13 is a drawing showing an embodiment of a tension regulator for use in regulating the tension at the two ends of the tension member of FIG. 11.

In FIG. 11, tension regulator 290" is shown as disposed on the lateral side of the left leg at point C" and comprises two ends of tension member 220". In alternative embodiments, regulator 290" may be placed elsewhere in tension member 220", such as, for example, above point F". Within regulator 290", as shown in more detail in FIG. 12, two outer strands 220a and 220c may be joined in order to form a single strand arranged to move freely on pulley 292". For the sake of clarity, some of the numbering used in FIG. 6 has been removed in FIG. 12 and only one end of tension member 220" is shown, the other end being identical but rotated by 180 degrees with respect to the one shown. Pulley 292" may rotate about pulley axis 294". Tension regulator 290" may be disposed on base 296" of substantially inextensible fabric with an inextensible direction parallel to strands 220A, 220B, and 220C of tension member 220". When tension member 220" comprises an odd number of strands, as in FIG. 12, the unpaired central strand may be terminated proximate or in tension regulator 290". Various ways are contemplated for terminating central strand 220B, and in FIG. 12 this is shown as general termination 298". FIG. 13 shows how both ends of tension member 220" may be terminated within tension regulator 290", with two pulleys 292" arranged head to head to balance the tension between strands 220A and 220C at the two ends of tension member 220". While a tension regulator at one end of tension member 220" may have the only one pulley 292", the fact that the tension regulator 292" of FIG. 11 has to regulate tension at two ends of tension member 220", implies that tension regulator 292" of FIG. 11 has the two-pulley arrangement of the tension regulator 292" of FIG. 13.

FIGS. 6B and 12 show only one pair of joined strands within tension member 220", but in general there may be a plurality of pairs of strands joined in this fashion. Such strands may be arranged in the generally symmetrical fashion shown in FIG. 12, each pair with a suitable pulley to balance the tension between the two joined strands in each pair. FIG. 12 shows on odd number of strands, namely three. In other embodiments the total number of strands in tension member 220" may be even, so that there are only joined pairs of strands. In general, the strands in the pairs are arranged to be joined such that the pairs are generally substantially mirror symmetrically disposed about the center line of the overall tension member. Each pair balances its tension between its two constituent strands by moving around a suitable pulley as described above.

In other embodiments, the regulator may have any other mechanical arrangement that allows the tension in two strands in a pair roughly equidistant from the center line of tension member 220" to be balanced. This includes, by way of non-limiting example, a curved tube (not shown) that allows the joined strands to slide freely within the curved tube.

In other embodiments, tension regulator 290" may be disposed proximate tensioner 240". In yet further embodiments, tension regulator 290" may be integrated into tensioner 240". In such an embodiment, the two pulley arrangements of FIG. 13 may be employed with the following modification. The regulating function is maintained by the rotation of the strands about the pulleys, while the tension may, by way of non-limiting example, be adjusted by moving the two pulley axes 294" toward or away from each other to respectively increase and decrease the tension. This allows the arrangement of FIG. 13 to function as an integrated combination of a tensioner and a tension regulator.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A garment arranged for enveloping at least in part an articulating joint of a human body, the articulating joint having at least one natural ligament, the garment comprising one or more tension members each disposed longitudinally along a corresponding predetermined curved three-dimensional spatial path within or on a matrix of a garment material, the corresponding predetermined paths spatially relating the one or more tension members to the at least one natural ligament of the joint, at least one of the tension members comprising a closed loop.

2. The garment of claim 1, wherein:
    the one or more tension members each comprises one or more strands of a substantially longitudinally inextensible material; and
    the garment comprises conduits disposed within or on the garment material and arranged to receive the one or more strands of each tension member.

3. The garment of claim 2, with the garment is configured for the articulating joint to be a knee with a patella in a leg of the human body, wherein the garment is configured so that the path of at least one of the one or more tension members comprises a lateral segment disposed to extend generally vertically proximate and lateral to the patella and a medial segment disposed to extend generally vertically proximate and medial to the patella.

4. The garment of claim 3, wherein the lateral and medial segments of the at least one tension member are further disposed to cross over each other above and below the knee at respectively upper and lower crossover points.

5. The garment of claim 4, further comprising at least one of a portion of inextensible fabric connecting the medial segment of the at least one tension member to the lateral segment of the at least one tension member and configured to extend over the anterior of the knee above the upper crossover point and a portion of inextensible fabric connecting the medial segment of the at least one tension member to the lateral segment of the at least one tension member over the anterior of the knee below the lower crossover point.

6. The garment of claim 3, further comprising at least one portion of inextensible fabric connecting the medial segment of the at least one tension member to the lateral segment of the at least one tension member around the posterior of the leg.

7. The garment of claim 2, wherein the tension members and the garment conduits each have respective coefficients of friction, and each conduit has a coefficient of friction lower than the coefficient of friction of the strands of the tension member.

8. The garment of claim 7, wherein each conduit comprises one or more tubes of material different from the garment material, the tubes arranged lengthwise along the predetermined three-dimensional spatial path of the corresponding tension member.

9. The garment of claim 2, further comprising at least one tensioner disposed in line with at least one of the one or more tension members for tensioning the at least one tension member.

10. The garment of claim 9, wherein at least one of the one or more tension members further comprises at least one tension regulator disposed for balancing tension differences between different strands of the at least one tension member.

11. The garment of claim 1, wherein the three-dimensional spatial path of at least one of the one or more tension members is configured to extend around a limb articulating at the joint.

12. The garment of claim 1, wherein the three-dimensional spatial path of at least one of the one or more tension members is arranged so that tension in the at least one tension member is configured to produce or exert a compressive force proximate the joint.

13. The garment of claim 1, wherein at least one longitudinal portion of the one or more tension members comprises a length of substantially inextensible fabric.

14. A garment wearable by a user, the garment comprising a closed tensionable loop and a tensioner disposed for tensioning the tensionable loop, the loop comprising a tension member made of a flexible and substantially longitudinally inextensible material arranged to freely move along a conduit within or on the garment, wherein:
the conduit is arranged to cross over itself between a lateral and a medial side on the anterior of a leg of the user at least one of above and below a knee of the leg;
the tensionable loop is disposed to apply pressure to at least one of a lateral collateral ligament and a medial collateral ligament of the user when the garment is worn by the user and the tensionable loop is tensioned.

15. The garment of claim 14, further comprising a belt disposed to fit around the waist of the user and wherein the tensionable loop is anchored to the belt.

16. The garment of claim 14, wherein the conduit is arranged along a path that circles the leg at a distal region of a triceps surae of the leg.

17. The garment of claim 14, further comprising an anchor member and wherein the tension member and the anchor member are jointly configured to at least partially encircle the thigh.

18. The garment of claim 14, wherein the tension member is configured to at least partially encircle the thigh.

19. A wearable garment for stabilizing a knee of a user comprising:
a closed tensionable loop arranged to freely move along a conduit disposed within or on the garment; and
an adjustable tensioner in or on the loop for adjusting a tension in the loop; wherein the conduit extends along a conduit path having, relative to the knee, a lateral portion and a medial portion passing a patella of the user knee proximate lateral and medial collateral ligaments of the user knee respectively;
the lateral and medial portions of the conduit path closely approach each other at least one point, the at least one point being at least one of below and above the user knee; and
the tensionable loop is disposed for applying pressure to at least one of the lateral collateral ligament and the medial collateral ligament of the user when the garment is worn by the user, and the tensionable loop is tensioned.

20. The garment of claim 19, wherein the conduit is arranged along a path that encircles the leg at a distal region of a triceps surae of the leg.

21. The garment of claim 19, wherein the tensionable loop comprises a tension member of a substantially longitudinally inextensible material extending along the conduit.

* * * * *